(12) United States Patent
Koo et al.

(10) Patent No.: US 9,287,091 B2
(45) Date of Patent: Mar. 15, 2016

(54) SYSTEM AND METHODS FOR PLASMA APPLICATION

(71) Applicant: COLORADO STATE UNIVERSITY RESEARCH FOUNDATION, Fort Collins, CO (US)

(72) Inventors: Il-Gyo Koo, Fort Collins, CO (US); Cameron A. Moore, Loveland, CO (US); George J. Collins, Fort Collins, CO (US); Jin-Hoon Cho, Savory, IL (US)

(73) Assignee: Colorado State University Research Foundation, Fort Collins, CO (US)

( * ) Notice: Subject to any disclaimer, the term of this patent is extended or adjusted under 35 U.S.C. 154(b) by 0 days.

(21) Appl. No.: 14/669,028

(22) Filed: Mar. 26, 2015

(65) Prior Publication Data

US 2015/0200076 A1   Jul. 16, 2015

Related U.S. Application Data

(63) Continuation of application No. 12/924,404, filed on Sep. 27, 2010, now Pat. No. 8,994,270, which is a continuation-in-part of application No. PCT/US2009/045708, filed on May 29, 2009.

(60) Provisional application No. 61/277,809, filed on Sep. 30, 2009, provisional application No. 61/057,667, filed on May 30, 2008.

(51) Int. Cl.
*H01J 37/32* (2006.01)
*H05H 1/24* (2006.01)

(52) U.S. Cl.
CPC ....... *H01J 37/32018* (2013.01); *H01J 37/3244* (2013.01); *H01J 37/32366* (2013.01);
(Continued)

(58) Field of Classification Search
USPC ........ 315/111.11–111.92; 606/41, 34, 45, 49, 606/50, 9, 101; 219/121.4–121.52
See application file for complete search history.

(56) References Cited

U.S. PATENT DOCUMENTS

| | | |
|---|---|---|
| 438,257 A | 10/1890 | Raquet |
| 2,213,820 A | 9/1940 | Maxson |

(Continued)

FOREIGN PATENT DOCUMENTS

| | | |
|---|---|---|
| DE | 3710489 A1 | 11/1987 |
| DE | 4139029 A1 | 6/1993 |

(Continued)

OTHER PUBLICATIONS

Japanese Notice of Final Rejection and Denial of Entry of Amendment (with English translation), issued Apr. 2, 2015, corresponding to Japanese Patent Application No. 2012-513022; 11 total pages.

(Continued)

*Primary Examiner* — Douglas W Owens
*Assistant Examiner* — Jonathan Cooper

(57) ABSTRACT

A plasma system includes a plasma device, an ionizable media source, and a power source. The plasma device includes an inner electrode and an outer electrode coaxially disposed around the inner electrode. The inner electrode includes a distal portion and an insulative layer that covers at least a portion of the inner electrode. The ionizable media source is coupled to the plasma device and is configured to supply ionizable media thereto. The power source is coupled to the inner and outer electrodes, and is configured to ignite the ionizable media at the plasma device to form a plasma effluent having an electron sheath layer about the exposed distal portion.

18 Claims, 15 Drawing Sheets

(52) U.S. Cl.
CPC ..... *H01J 37/32449* (2013.01); *H01J 37/32541* (2013.01); *H01J 37/32559* (2013.01); *H01J 37/32568* (2013.01); *H01J 37/32577* (2013.01); *H05H 1/24* (2013.01); *H05H 1/2406* (2013.01); *H01J 2237/332* (2013.01); *H01J 2237/334* (2013.01); *H05H 2001/2412* (2013.01); *H05H 2001/2431* (2013.01); *H05H 2001/2443* (2013.01); *H05H 2245/122* (2013.01)

(56) References Cited

U.S. PATENT DOCUMENTS

| | | | |
|---|---|---|---|
| 2,598,301 | A | 5/1952 | Rajchman |
| 3,134,947 | A | 5/1964 | Charasz |
| 3,434,476 | A | 3/1969 | Shaw et al. |
| 3,671,195 | A | 6/1972 | Bersin |
| 3,838,242 | A | 9/1974 | Goucher |
| 3,903,891 | A | 9/1975 | Brayshaw |
| 3,938,525 | A | 2/1976 | Coucher |
| 3,991,764 | A | 11/1976 | Incropera et al. |
| 4,010,400 | A | 3/1977 | Hollister |
| 4,017,707 | A | 4/1977 | Brown et al. |
| 4,143,337 | A | 3/1979 | Beaulieu |
| 4,177,422 | A | 12/1979 | Deficis et al. |
| 4,181,897 | A | 1/1980 | Miller |
| 4,188,426 | A | 2/1980 | Auerbach |
| 4,274,919 | A | 6/1981 | Jensen et al. |
| 4,337,415 | A | 6/1982 | Durr |
| 4,577,165 | A | 3/1986 | Uehara et al. |
| 4,629,887 | A | 12/1986 | Bernier |
| 4,629,940 | A | 12/1986 | Gagne et al. |
| 4,780,803 | A | 10/1988 | Dede Garcia-Santamaria |
| 4,781,175 | A | 11/1988 | McGreevy et al. |
| 4,818,916 | A | 4/1989 | Morrisroe |
| 4,877,999 | A | 10/1989 | Knapp et al. |
| 4,901,719 | A | 2/1990 | Trenconsky et al. |
| 4,922,210 | A | 5/1990 | Flachenecker et al. |
| 4,956,582 | A | 9/1990 | Bourassa |
| 5,025,373 | A | 6/1991 | Keyser, Jr. et al. |
| 5,041,110 | A | 8/1991 | Fleenor |
| 5,088,997 | A | 2/1992 | Delahuerga et al. |
| 5,098,430 | A | 3/1992 | Fleenor |
| 5,117,088 | A | 5/1992 | Stava |
| 5,124,526 | A | 6/1992 | Muller et al. |
| 5,135,604 | A | 8/1992 | Kumar et al. |
| 5,155,547 | A | 10/1992 | Casper et al. |
| 5,159,173 | A | 10/1992 | Frind et al. |
| 5,180,949 | A | 1/1993 | Durr |
| 5,217,457 | A | 6/1993 | Delahuerga et al. |
| 5,223,457 | A | 6/1993 | Mintz et al. |
| 5,256,138 | A | 10/1993 | Burek et al. |
| 5,280,154 | A | 1/1994 | Cuomo et al. |
| 5,300,068 | A | 4/1994 | Rosar et al. |
| 5,304,279 | A | 4/1994 | Coultas et al. |
| 5,320,621 | A | 6/1994 | Gordon et al. |
| 5,334,834 | A | 8/1994 | Ito et al. |
| RE34,780 | E | 11/1994 | Trenconsky et al. |
| 5,383,019 | A | 1/1995 | Farrell et al. |
| 5,384,167 | A | 1/1995 | Nishiwaki et al. |
| 5,401,350 | A | 3/1995 | Patrick et al. |
| 5,449,356 | A | 9/1995 | Walbrink et al. |
| 5,449,432 | A | 9/1995 | Hanawa |
| 5,505,729 | A | 4/1996 | Rau |
| 5,526,138 | A | 6/1996 | Sato |
| 5,534,231 | A | 7/1996 | Savas |
| 5,554,172 | A | 9/1996 | Horner et al. |
| 5,607,509 | A | 3/1997 | Schumacher et al. |
| 5,618,382 | A | 4/1997 | Mintz et al. |
| 5,656,186 | A | 8/1997 | Mourou et al. |
| 5,669,904 | A | 9/1997 | Platt, Jr. et al. |
| 5,669,907 | A | 9/1997 | Platt, Jr. et al. |
| 5,683,366 | A | 11/1997 | Eggers et al. |
| 5,688,357 | A | 11/1997 | Hanawa |
| 5,697,882 | A | 12/1997 | Eggers et al. |
| 5,707,402 | A | 1/1998 | Heim |
| 5,708,330 | A | 1/1998 | Rothenbuhler et al. |
| 5,720,745 | A | 2/1998 | Farin et al. |
| 5,733,511 | A | 3/1998 | De Francesco |
| 5,810,764 | A | 9/1998 | Eggers et al. |
| 5,818,581 | A | 10/1998 | Kurosawa et al. |
| 5,841,531 | A | 11/1998 | Gliddon |
| 5,843,019 | A | 12/1998 | Eggers et al. |
| 5,843,079 | A | 12/1998 | Suslov |
| 5,845,488 | A | 12/1998 | Hancock et al. |
| 5,849,136 | A | 12/1998 | Mintz et al. |
| 5,858,477 | A | 1/1999 | Veerasamy et al. |
| 5,865,937 | A | 2/1999 | Shan et al. |
| 5,866,871 | A | 2/1999 | Birx |
| 5,866,985 | A | 2/1999 | Coultas et al. |
| 5,892,328 | A | 4/1999 | Shang et al. |
| 5,909,086 | A | 6/1999 | Kim et al. |
| 5,961,772 | A | 10/1999 | Selwyn |
| 5,977,715 | A | 11/1999 | Li et al. |
| 6,013,075 | A | 1/2000 | Avramenko et al. |
| 6,020,794 | A | 2/2000 | Wilbur |
| 6,024,733 | A | 2/2000 | Eggers et al. |
| 6,027,601 | A | 2/2000 | Hanawa |
| 6,030,667 | A | 2/2000 | Nakagawa et al. |
| 6,033,582 | A | 3/2000 | Lee et al. |
| 6,036,878 | A | 3/2000 | Collins |
| 6,046,546 | A | 4/2000 | Porter et al. |
| 6,047,700 | A | 4/2000 | Eggers et al. |
| 6,053,172 | A | 4/2000 | Hovda et al. |
| 6,063,079 | A | 5/2000 | Hovda et al. |
| 6,063,084 | A | 5/2000 | Farin |
| 6,063,937 | A | 5/2000 | Dlubala et al. |
| 6,066,134 | A | 5/2000 | Eggers et al. |
| 6,086,585 | A | 7/2000 | Hovda et al. |
| 6,099,523 | A | 8/2000 | Kim et al. |
| 6,102,046 | A | 8/2000 | Weinstein et al. |
| 6,105,581 | A | 8/2000 | Eggers et al. |
| 6,109,268 | A | 8/2000 | Thapliyal et al. |
| 6,110,395 | A | 8/2000 | Gibson, Jr. |
| 6,113,597 | A | 9/2000 | Eggers et al. |
| 6,132,575 | A | 10/2000 | Pandumsoporn et al. |
| 6,137,237 | A | 10/2000 | MacLennan et al. |
| 6,142,992 | A | 11/2000 | Cheng et al. |
| 6,149,620 | A | 11/2000 | Baker et al. |
| 6,153,852 | A | 11/2000 | Blutke et al. |
| 6,159,208 | A | 12/2000 | Hovda et al. |
| 6,159,531 | A | 12/2000 | Dang et al. |
| 6,170,428 | B1 | 1/2001 | Redeker et al. |
| 6,172,130 | B1 | 1/2001 | Bellesort |
| 6,172,324 | B1 | 1/2001 | Birx |
| 6,178,918 | B1 | 1/2001 | van Os et al. |
| 6,179,836 | B1 | 1/2001 | Eggers et al. |
| 6,182,469 | B1 | 2/2001 | Campbell et al. |
| 6,183,655 | B1 | 2/2001 | Wang et al. |
| 6,190,381 | B1 | 2/2001 | Olsen et al. |
| 6,197,026 | B1 | 3/2001 | Farin et al. |
| 6,203,542 | B1 | 3/2001 | Ellsberry et al. |
| 6,206,871 | B1 | 3/2001 | Zanon et al. |
| 6,206,878 | B1 | 3/2001 | Bishop et al. |
| 6,207,924 | B1 | 3/2001 | Trassy |
| 6,210,402 | B1 | 4/2001 | Olsen et al. |
| 6,210,410 | B1 | 4/2001 | Farin et al. |
| 6,213,999 | B1 | 4/2001 | Platt, Jr. et al. |
| 6,222,186 | B1 | 4/2001 | Li et al. |
| 6,224,592 | B1 | 5/2001 | Eggers et al. |
| 6,225,593 | B1 | 5/2001 | Howieson et al. |
| 6,228,078 | B1 | 5/2001 | Eggers et al. |
| 6,228,082 | B1 | 5/2001 | Baker et al. |
| 6,228,229 | B1 | 5/2001 | Raaijmakers et al. |
| 6,235,020 | B1 | 5/2001 | Cheng et al. |
| 6,237,526 | B1 | 5/2001 | Brcka |
| 6,238,391 | B1 | 5/2001 | Olsen et al. |
| 6,242,735 | B1 | 6/2001 | Li et al. |
| 6,248,250 | B1 | 6/2001 | Hanawa et al. |
| 6,252,354 | B1 | 6/2001 | Collins et al. |
| 6,254,600 | B1 | 7/2001 | Willink et al. |
| 6,254,738 | B1 | 7/2001 | Stimson et al. |
| 6,264,650 | B1 | 7/2001 | Hovda et al. |
| 6,264,651 | B1 | 7/2001 | Underwood et al. |
| 6,264,652 | B1 | 7/2001 | Eggers et al. |

(56) References Cited

U.S. PATENT DOCUMENTS

| | | |
|---|---|---|
| 6,270,687 B1 | 8/2001 | Ye et al. |
| 6,277,112 B1 | 8/2001 | Underwood et al. |
| 6,277,251 B1 | 8/2001 | Hwang et al. |
| 6,283,961 B1 | 9/2001 | Underwood et al. |
| 6,287,980 B1 | 9/2001 | Hanazaki et al. |
| 6,291,938 B1 | 9/2001 | Jewett et al. |
| 6,296,636 B1 | 10/2001 | Cheng et al. |
| 6,296,638 B1 | 10/2001 | Davison et al. |
| 6,299,948 B1 | 10/2001 | Gherardi et al. |
| 6,309,387 B1 | 10/2001 | Eggers et al. |
| 6,313,587 B1 | 11/2001 | MacLennan et al. |
| 6,326,584 B1 | 12/2001 | Jewett et al. |
| 6,326,739 B1 | 12/2001 | MacLennan et al. |
| 6,328,760 B1 | 12/2001 | James |
| 6,329,757 B1 | 12/2001 | Morrisroe et al. |
| 6,333,481 B2 | 12/2001 | Augeraud et al. |
| 6,345,588 B1 | 2/2002 | Stimson |
| 6,346,108 B1 | 2/2002 | Fischer |
| 6,348,051 B1 | 2/2002 | Farin et al. |
| 6,353,206 B1 | 3/2002 | Roderick |
| 6,355,032 B1 | 3/2002 | Hovda et al. |
| 6,363,937 B1 | 4/2002 | Hovda et al. |
| 6,365,063 B2 | 4/2002 | Collins et al. |
| 6,375,750 B1 | 4/2002 | van Os et al. |
| 6,379,351 B1 | 4/2002 | Thapliyal et al. |
| 6,387,088 B1 | 5/2002 | Shattuck et al. |
| 6,391,025 B1 | 5/2002 | Weinstein et al. |
| 6,396,214 B1 | 5/2002 | Grosse et al. |
| 6,401,652 B1 | 6/2002 | Mohn et al. |
| 6,409,933 B1 | 6/2002 | Holland et al. |
| RE37,780 E | 7/2002 | Lanzani et al. |
| 6,416,507 B1 | 7/2002 | Eggers et al. |
| 6,416,508 B1 | 7/2002 | Eggers et al. |
| 6,416,633 B1 | 7/2002 | Spence |
| 6,424,099 B1 | 7/2002 | Kirkpatrick et al. |
| 6,424,232 B1 | 7/2002 | Mavretic et al. |
| 6,432,103 B1 | 8/2002 | Ellsberry et al. |
| 6,432,260 B1 | 8/2002 | Mahoney et al. |
| 6,443,948 B1 | 9/2002 | Suslov |
| 6,444,084 B1 | 9/2002 | Collins |
| 6,445,141 B1 | 9/2002 | Kastner et al. |
| 6,459,066 B1 | 10/2002 | Khater et al. |
| 6,461,350 B1 | 10/2002 | Underwood et al. |
| 6,461,354 B1 | 10/2002 | Olsen et al. |
| 6,464,695 B2 | 10/2002 | Hovda et al. |
| 6,464,889 B1 | 10/2002 | Lee et al. |
| 6,464,891 B1 | 10/2002 | Druz et al. |
| 6,468,270 B1 | 10/2002 | Hovda et al. |
| 6,468,274 B1 | 10/2002 | Alleyne et al. |
| 6,471,822 B1 | 10/2002 | Yin et al. |
| 6,474,258 B2 | 11/2002 | Brcka |
| 6,475,217 B1 | 11/2002 | Platt |
| 6,482,201 B1 | 11/2002 | Olsen et al. |
| 6,497,826 B2 | 12/2002 | Li et al. |
| 6,500,173 B2 | 12/2002 | Underwood et al. |
| 6,502,416 B2 | 1/2003 | Kawasumi et al. |
| 6,502,588 B2 | 1/2003 | Li et al. |
| 6,507,155 B1 | 1/2003 | Barnes et al. |
| 6,525,481 B1 | 2/2003 | Klima et al. |
| 6,534,133 B1 | 3/2003 | Kaloyeros et al. |
| 6,540,741 B1 | 4/2003 | Underwood et al. |
| 6,544,261 B2 | 4/2003 | Ellsberry et al. |
| 6,558,383 B2 | 5/2003 | Cunningham et al. |
| 6,565,558 B1 | 5/2003 | Lindenmeier et al. |
| 6,575,968 B1 | 6/2003 | Eggers et al. |
| 6,579,289 B2 | 6/2003 | Schnitzler |
| 6,579,426 B1 | 6/2003 | van Gogh et al. |
| 6,582,423 B1 | 6/2003 | Thapliyal et al. |
| 6,582,427 B1 | 6/2003 | Goble et al. |
| 6,582,429 B2 | 6/2003 | Krishnan et al. |
| 6,589,237 B2 | 7/2003 | Woloszko et al. |
| 6,589,437 B1 | 7/2003 | Collins |
| 6,595,990 B1 | 7/2003 | Weinstein et al. |
| 6,617,794 B2 | 9/2003 | Barnes et al. |
| 6,624,583 B1 | 9/2003 | Coll et al. |
| 6,625,555 B2 | 9/2003 | Kuan et al. |
| 6,629,974 B2 | 10/2003 | Penny et al. |
| 6,632,193 B1 | 10/2003 | Davison et al. |
| 6,632,220 B1 | 10/2003 | Eggers et al. |
| 6,642,526 B2 | 11/2003 | Hartley |
| 6,646,386 B1 | 11/2003 | Sirkis et al. |
| 6,652,717 B1 | 11/2003 | Hong |
| 6,653,594 B2 | 11/2003 | Nakamura et al. |
| 6,657,594 B2 | 12/2003 | Anderson |
| 6,659,106 B1 | 12/2003 | Hovda et al. |
| 6,663,017 B2 | 12/2003 | Endres et al. |
| 6,666,865 B2 | 12/2003 | Platt |
| 6,685,803 B2 | 2/2004 | Lazarovich et al. |
| 6,712,811 B2 | 3/2004 | Underwood et al. |
| 6,719,754 B2 | 4/2004 | Underwood et al. |
| 6,719,883 B2 | 4/2004 | Stimson |
| 6,723,091 B2 | 4/2004 | Goble et al. |
| 6,726,684 B1 | 4/2004 | Woloszko et al. |
| 6,740,842 B2 | 5/2004 | Johnson et al. |
| 6,746,447 B2 | 6/2004 | Davison et al. |
| 6,763,836 B2 | 7/2004 | Tasto et al. |
| 6,770,071 B2 | 8/2004 | Woloszko et al. |
| 6,772,012 B2 | 8/2004 | Ricart et al. |
| 6,773,431 B2 | 8/2004 | Eggers et al. |
| 6,774,569 B2 | 8/2004 | de Vries et al. |
| 6,780,178 B2 | 8/2004 | Palanker et al. |
| 6,780,184 B2 | 8/2004 | Tanrisever |
| 6,781,317 B1 | 8/2004 | Goodman |
| 6,787,730 B2 | 9/2004 | Coccio et al. |
| 6,805,130 B2 | 10/2004 | Tasto et al. |
| 6,806,438 B2 | 10/2004 | Nakano et al. |
| 6,815,633 B1 | 11/2004 | Chen et al. |
| 6,818,140 B2 | 11/2004 | Ding |
| 6,832,996 B2 | 12/2004 | Woloszko et al. |
| 6,837,884 B2 | 1/2005 | Woloszko |
| 6,837,887 B2 | 1/2005 | Woloszko et al. |
| 6,837,888 B2 | 1/2005 | Ciarrocca et al. |
| 6,840,937 B2 | 1/2005 | Van Wyk |
| 6,849,191 B2 | 2/2005 | Ono et al. |
| 6,852,112 B2 | 2/2005 | Platt |
| 6,855,143 B2 | 2/2005 | Davison et al. |
| 6,855,225 B1 | 2/2005 | Su et al. |
| 6,861,377 B1 | 3/2005 | Hirai et al. |
| 6,867,859 B1 | 3/2005 | Powell |
| 6,876,155 B2 | 4/2005 | Howald et al. |
| 6,890,332 B2 | 5/2005 | Truckai et al. |
| 6,896,672 B1 | 5/2005 | Eggers et al. |
| 6,896,674 B1 | 5/2005 | Woloszko et al. |
| 6,896,775 B2 | 5/2005 | Chistyakov |
| 6,909,237 B1 | 6/2005 | Park et al. |
| 6,911,029 B2 | 6/2005 | Platt |
| 6,915,806 B2 | 7/2005 | Pacek et al. |
| 6,919,527 B2 | 7/2005 | Boulos et al. |
| 6,920,883 B2 | 7/2005 | Bessette et al. |
| 6,921,398 B2 | 7/2005 | Carmel et al. |
| 6,922,093 B2 | 7/2005 | Kanda |
| 6,924,455 B2 | 8/2005 | Chen et al. |
| 6,929,640 B1 | 8/2005 | Underwood et al. |
| 6,949,096 B2 | 9/2005 | Davison et al. |
| 6,949,887 B2 | 9/2005 | Kirkpatrick et al. |
| 6,958,063 B1 | 10/2005 | Soll et al. |
| 6,974,453 B2 | 12/2005 | Woloszko et al. |
| 6,991,631 B2 | 1/2006 | Woloszko et al. |
| 7,004,941 B2 | 2/2006 | Tvinnereim et al. |
| 7,019,253 B2 | 3/2006 | Johnson et al. |
| 7,046,088 B2 | 5/2006 | Ziegler |
| 7,048,733 B2 | 5/2006 | Hartley et al. |
| 7,070,596 B1 | 7/2006 | Woloszko et al. |
| 7,084,832 B2 | 8/2006 | Pribyl |
| 7,090,672 B2 | 8/2006 | Underwood et al. |
| 7,096,819 B2 | 8/2006 | Chen et al. |
| 7,100,532 B2 | 9/2006 | Pribyl |
| 7,104,986 B2 | 9/2006 | Hovda et al. |
| 7,115,185 B1 | 10/2006 | Gonzalez et al. |
| 7,122,035 B2 | 10/2006 | Canady |
| 7,122,965 B2 | 10/2006 | Goodman |
| 7,131,969 B1 | 11/2006 | Hovda et al. |
| 7,132,620 B2 | 11/2006 | Coelho et al. |
| 7,132,996 B2 | 11/2006 | Evans et al. |

(56) References Cited

U.S. PATENT DOCUMENTS

| | | |
|---|---|---|
| 7,150,745 B2 | 12/2006 | Stern et al. |
| 7,157,857 B2 | 1/2007 | Brouk et al. |
| 7,160,521 B2 | 1/2007 | Porshnev et al. |
| 7,161,112 B2 | 1/2007 | Smith et al. |
| 7,164,484 B2 | 1/2007 | Takahashi et al. |
| 7,165,451 B1 | 1/2007 | Brooks et al. |
| 7,166,816 B1 | 1/2007 | Chen et al. |
| 7,179,255 B2 | 2/2007 | Lettice et al. |
| 7,186,234 B2 | 3/2007 | Dahla et al. |
| 7,189,939 B2 | 3/2007 | Lee et al. |
| 7,189,940 B2 | 3/2007 | Kumar et al. |
| 7,192,428 B2 | 3/2007 | Eggers et al. |
| 7,199,399 B2 | 4/2007 | Chin-Lung et al. |
| 7,201,750 B1 | 4/2007 | Eggers et al. |
| 7,214,280 B2 | 5/2007 | Kumar et al. |
| 7,214,934 B2 | 5/2007 | Stevenson |
| 7,217,268 B2 | 5/2007 | Eggers et al. |
| 7,217,903 B2 | 5/2007 | Bayer et al. |
| 7,220,261 B2 | 5/2007 | Truckai et al. |
| 7,227,097 B2 | 6/2007 | Kumar et al. |
| 7,238,185 B2 | 7/2007 | Palanker et al. |
| 7,241,293 B2 | 7/2007 | Davison |
| 7,270,658 B2 | 9/2007 | Woloszko et al. |
| 7,270,659 B2 | 9/2007 | Ricart et al. |
| 7,270,661 B2 | 9/2007 | Dahla et al. |
| 7,271,363 B2 | 9/2007 | Lee et al. |
| 7,275,344 B2 | 10/2007 | Woodmansee, III et al. |
| 7,276,063 B2 | 10/2007 | Davison et al. |
| 7,282,244 B2 | 10/2007 | Schaepkens et al. |
| 7,292,191 B2 | 11/2007 | Anderson |
| 7,297,143 B2 | 11/2007 | Woloszko et al. |
| 7,297,145 B2 | 11/2007 | Woloszko et al. |
| 7,298,091 B2 | 11/2007 | Pickard et al. |
| 7,309,843 B2 | 12/2007 | Kumar et al. |
| 7,311,708 B2 | 12/2007 | McClurken |
| 7,316,682 B2 | 1/2008 | Konesky |
| 7,318,823 B2 | 1/2008 | Sharps et al. |
| 7,331,957 B2 | 2/2008 | Woloszko et al. |
| 7,353,771 B2 | 4/2008 | Millner et al. |
| 7,355,379 B2 | 4/2008 | Kitamura et al. |
| 7,357,798 B2 | 4/2008 | Sharps et al. |
| 7,361,175 B2 | 4/2008 | Suslov |
| 7,382,129 B2 | 6/2008 | Mills |
| 7,387,625 B2 | 6/2008 | Hovda et al. |
| 7,393,351 B2 | 7/2008 | Woloszko et al. |
| 7,399,944 B2 | 7/2008 | DeVries et al. |
| 7,410,669 B2 | 8/2008 | Dieckhoff et al. |
| 7,419,488 B2 | 9/2008 | Ciarrocca et al. |
| 7,426,900 B2 | 9/2008 | Brcka |
| 7,429,260 B2 | 9/2008 | Underwood et al. |
| 7,429,262 B2 | 9/2008 | Woloszko et al. |
| 7,431,857 B2 | 10/2008 | Shannon et al. |
| 7,435,247 B2 | 10/2008 | Woloszko et al. |
| 7,442,191 B2 | 10/2008 | Hovda et al. |
| 7,445,619 B2 | 11/2008 | Auge, II et al. |
| 7,449,021 B2 | 11/2008 | Underwood et al. |
| 7,453,403 B2 | 11/2008 | Anderson |
| 7,458,973 B2 | 12/2008 | Ouchi |
| 7,459,899 B2 | 12/2008 | Mattaboni et al. |
| 7,468,059 B2 | 12/2008 | Eggers et al. |
| 7,480,299 B2 | 1/2009 | O'Keeffe et al. |
| 7,489,206 B2 | 2/2009 | Kotani et al. |
| 7,491,200 B2 | 2/2009 | Underwood |
| 7,497,119 B2 | 3/2009 | Brooks et al. |
| 7,498,000 B2 | 3/2009 | Pekshev et al. |
| 7,506,014 B2 | 3/2009 | Drummond |
| 7,507,236 B2 | 3/2009 | Eggers et al. |
| 7,510,665 B2 | 3/2009 | Shannon et al. |
| 7,511,246 B2 | 3/2009 | Morrisroe |
| 7,549,990 B2 | 6/2009 | Canady |
| 7,563,261 B2 | 7/2009 | Carmel et al. |
| 7,566,333 B2 | 7/2009 | Van Wyk et al. |
| 7,572,255 B2 | 8/2009 | Sartor et al. |
| 7,578,817 B2 | 8/2009 | Canady |
| 7,578,818 B2 | 8/2009 | Platt |
| 7,589,473 B2 | 9/2009 | Suslov |
| 7,601,150 B2 | 10/2009 | Farin |
| 7,608,839 B2 | 10/2009 | Coulombe et al. |
| 7,611,509 B2 | 11/2009 | Van Wyk |
| 7,628,787 B2 | 12/2009 | Sartor et al. |
| 7,632,267 B2 | 12/2009 | Dahla |
| 7,633,231 B2 | 12/2009 | Watson |
| 7,648,503 B2 | 1/2010 | Podhajsky |
| 7,666,478 B2 | 2/2010 | Paulussen et al. |
| 7,691,101 B2 | 4/2010 | Davison et al. |
| 7,691,102 B2 | 4/2010 | Podhajsky et al. |
| 7,708,733 B2 | 5/2010 | Sanders et al. |
| 7,715,889 B2 | 5/2010 | Ito |
| 7,758,575 B2 | 7/2010 | Beller |
| 7,824,398 B2 | 11/2010 | Woloszko et al. |
| 7,879,034 B2 | 2/2011 | Woloszko et al. |
| 7,887,891 B2 | 2/2011 | Rius |
| 7,892,223 B2 | 2/2011 | Geiselhart |
| 7,892,230 B2 | 2/2011 | Woloszko |
| 7,901,403 B2 | 3/2011 | Woloszko et al. |
| 7,940,008 B2 | 5/2011 | Mattaboni et al. |
| 7,949,407 B2 | 5/2011 | Kaplan et al. |
| 8,994,270 B2 | 3/2015 | Koo et al. |
| 2001/0025177 A1 | 9/2001 | Woloszko et al. |
| 2001/0054601 A1 | 12/2001 | Ding |
| 2002/0014832 A1 | 2/2002 | Moradi et al. |
| 2002/0022836 A1 | 2/2002 | Goble et al. |
| 2002/0022838 A1 | 2/2002 | Cunningham et al. |
| 2002/0023899 A1 | 2/2002 | Khater et al. |
| 2002/0092826 A1 | 7/2002 | Ding |
| 2002/0125207 A1 | 9/2002 | Ono et al. |
| 2002/0132380 A1 | 9/2002 | Nakano et al. |
| 2003/0006019 A1 | 1/2003 | Johnson et al. |
| 2003/0008327 A1 | 1/2003 | Ornatskaia |
| 2003/0027186 A1 | 2/2003 | Pierce |
| 2003/0036753 A1 | 2/2003 | Morgan et al. |
| 2003/0075522 A1 | 4/2003 | Weichart et al. |
| 2003/0093073 A1 | 5/2003 | Platt |
| 2003/0105456 A1 | 6/2003 | Lin |
| 2003/0132198 A1 | 7/2003 | Ono et al. |
| 2003/0158545 A1 | 8/2003 | Hovda et al. |
| 2003/0208194 A1 | 11/2003 | Hovda et al. |
| 2004/0007985 A1 | 1/2004 | de Vries et al. |
| 2004/0022669 A1 | 2/2004 | Ruan et al. |
| 2004/0027127 A1 | 2/2004 | Mills |
| 2004/0075375 A1 | 4/2004 | Miyashita et al. |
| 2004/0086434 A1 | 5/2004 | Gadgil et al. |
| 2004/0111219 A1 | 6/2004 | Gulati |
| 2004/0116918 A1 | 6/2004 | Konesky |
| 2004/0129212 A1 | 7/2004 | Gadgil et al. |
| 2004/0138658 A1 | 7/2004 | Farin et al. |
| 2004/0140194 A1 | 7/2004 | Taylor et al. |
| 2004/0181220 A1 | 9/2004 | Farin |
| 2005/0015001 A1 | 1/2005 | Lec et al. |
| 2005/0017646 A1 | 1/2005 | Boulos et al. |
| 2005/0080413 A1 | 4/2005 | Canady |
| 2005/0103748 A1 | 5/2005 | Yamaguchi et al. |
| 2005/0107786 A1 | 5/2005 | Canady |
| 2005/0118350 A1 | 6/2005 | Koulik et al. |
| 2005/0149012 A1 | 7/2005 | Penny et al. |
| 2005/0205212 A1 | 9/2005 | Singh et al. |
| 2006/0004354 A1 | 1/2006 | Suslov |
| 2006/0011465 A1 | 1/2006 | Burke et al. |
| 2006/0017388 A1 | 1/2006 | Stevenson |
| 2006/0036239 A1 | 2/2006 | Canady |
| 2006/0038992 A1 | 2/2006 | Morrisroe |
| 2006/0052771 A1 | 3/2006 | Sartor et al. |
| 2006/0065628 A1 | 3/2006 | Vahedi et al. |
| 2006/0084154 A1 | 4/2006 | Jones et al. |
| 2006/0127879 A1 | 6/2006 | Fuccione |
| 2006/0172429 A1 | 8/2006 | Nilsson et al. |
| 2006/0175015 A1 | 8/2006 | Chen et al. |
| 2006/0200122 A1 | 9/2006 | Sartor et al. |
| 2006/0224146 A1 | 10/2006 | Lin |
| 2006/0266735 A1 | 11/2006 | Shannon et al. |
| 2006/0278254 A1 | 12/2006 | Jackson |
| 2007/0014752 A1 | 1/2007 | Roy et al. |
| 2007/0021747 A1 | 1/2007 | Suslov |
| 2007/0021748 A1 | 1/2007 | Suslov |

(56) References Cited

U.S. PATENT DOCUMENTS

| | | | |
|---|---|---|---|
| 2007/0029292 | A1 | 2/2007 | Suslov et al. |
| 2007/0029500 | A1 | 2/2007 | Coulombe et al. |
| 2007/0039389 | A1 | 2/2007 | Brooks et al. |
| 2007/0084563 | A1 | 4/2007 | Holland |
| 2007/0087455 | A1 | 4/2007 | Hoffman |
| 2007/0149970 | A1 | 6/2007 | Schnitzler et al. |
| 2007/0210035 | A1 | 9/2007 | Twarog et al. |
| 2007/0213704 | A1 | 9/2007 | Truckai et al. |
| 2007/0251920 | A1 | 11/2007 | Hoffman |
| 2007/0255271 | A1 | 11/2007 | Dabney et al. |
| 2007/0258329 | A1 | 11/2007 | Winey |
| 2007/0282322 | A1 | 12/2007 | Dabney et al. |
| 2007/0292972 | A1 | 12/2007 | Paulussen et al. |
| 2008/0023443 | A1 | 1/2008 | Paterson et al. |
| 2008/0039832 | A1 | 2/2008 | Palanker et al. |
| 2008/0050291 | A1 | 2/2008 | Nagasawa |
| 2008/0083701 | A1 | 4/2008 | Shao et al. |
| 2008/0099434 | A1 | 5/2008 | Chandrachood et al. |
| 2008/0099435 | A1 | 5/2008 | Grimbergen |
| 2008/0099436 | A1 | 5/2008 | Grimbergen |
| 2008/0108985 | A1 | 5/2008 | Konesky |
| 2008/0122252 | A1 | 5/2008 | Corke et al. |
| 2008/0122368 | A1* | 5/2008 | Saito et al. ............... 315/111.21 |
| 2008/0167398 | A1 | 7/2008 | Patil et al. |
| 2008/0179290 | A1 | 7/2008 | Collins et al. |
| 2008/0185366 | A1 | 8/2008 | Suslov |
| 2008/0268172 | A1 | 10/2008 | Fukuda et al. |
| 2008/0284506 | A1 | 11/2008 | Messer |
| 2008/0292497 | A1 | 11/2008 | Vangeneugden et al. |
| 2009/0039789 | A1 | 2/2009 | Nikolay |
| 2009/0048594 | A1 | 2/2009 | Sartor et al. |
| 2009/0054893 | A1 | 2/2009 | Sartor et al. |
| 2009/0054896 | A1 | 2/2009 | Fridman et al. |
| 2009/0064933 | A1 | 3/2009 | Liu et al. |
| 2009/0076505 | A1 | 3/2009 | Arts |
| 2009/0206757 | A1* | 8/2009 | Masuda et al. ........... 315/111.21 |
| 2009/0216226 | A1 | 8/2009 | Davison et al. |
| 2009/0275941 | A1 | 11/2009 | Sartor et al. |
| 2010/0016856 | A1 | 1/2010 | Platt, Jr. |
| 2010/0042094 | A1 | 2/2010 | Arts |
| 2010/0069902 | A1 | 3/2010 | Sartor et al. |
| 2010/0089742 | A1 | 4/2010 | Suslov |
| 2010/0114096 | A1 | 5/2010 | Podhajsky |
| 2010/0125267 | A1* | 5/2010 | Lee et al. ........................ 606/27 |
| 2010/0130973 | A1 | 5/2010 | Choi et al. |

FOREIGN PATENT DOCUMENTS

| | | | |
|---|---|---|---|
| DE | 4326037 | A1 | 2/1995 |
| DE | 9117019 | U1 | 3/1995 |
| DE | 19524646 | A1 | 2/1997 |
| DE | 19537897 | A1 | 3/1997 |
| DE | 9117299 | U1 | 3/2000 |
| DE | 19848784 | A1 | 5/2000 |
| DE | 29724247 | U1 | 8/2000 |
| EP | 0016542 | A2 | 10/1980 |
| EP | 0495699 | A1 | 7/1992 |
| EP | 0602764 | A1 | 6/1994 |
| EP | 0956827 | A1 | 11/1999 |
| EP | 1174901 | A2 | 1/2002 |
| FR | 1340509 | A | 10/1963 |
| JP | 61-159953 | A | 7/1986 |
| JP | 62-130777 | | 6/1987 |
| JP | 03-149797 | | 6/1991 |
| JP | 8-243755 | | 9/1996 |
| JP | 2000286094 | A | 10/2000 |
| JP | 2001332399 | A | 11/2001 |
| JP | 2003093869 | A | 4/2003 |
| JP | 2005-522824 | A | 7/2005 |
| JP | 2005276618 | A | 10/2005 |
| JP | 2006114450 | A | 4/2006 |
| JP | 2006310101 | A | 11/2006 |
| JP | 2007188748 | A | 7/2007 |
| JP | 2007207540 | A | 8/2007 |
| JP | 2008041495 | A | 2/2008 |
| JP | 2008071656 | A | 3/2008 |
| JP | 2010-242857 | A | 10/2010 |
| KR | WO/2004032176 | * | 4/2004 |
| SU | 1438745 | A1 | 11/1988 |
| WO | 9901887 | A1 | 1/1999 |
| WO | 9936940 | A2 | 7/1999 |
| WO | 0139555 | A1 | 5/2001 |
| WO | 03/085693 | A1 | 10/2003 |
| WO | 2004032176 | A1 | 4/2004 |
| WO | 2004094306 | A1 | 11/2004 |
| WO | 2006116252 | A2 | 11/2006 |
| WO | 2009/146432 | A1 | 12/2009 |
| WO | 2009146439 | A1 | 12/2009 |
| WO | 2010008062 | A1 | 1/2010 |

OTHER PUBLICATIONS

Sobolewski, Mark A., "Current and Voltage Measurements in the Gaseous Electronics Conference RF Reference Cell," J. Res. Natl. Inst. Stand. Technol., vol. 100, No. 4, pp. 341-351 (1995).

International Search Report and Written Opinion from Int'l Appl. No. PCT/US2009/005398 mailed Apr. 5, 2010.

International Search Report and Written Opinion from Int'l Appl. No. PCT/US2009/005389 mailed Oct. 26, 2009.

U.S. Appl. No. 08/383,162, filed Feb. 3, 1995, Lawrence K. Pacer.

U.S. Appl. No. 08/619,380, filed Mar. 21, 1996, Gene H. Arts.

U.S. Appl. No. 08/621,151, filed Mar. 21, 1996, Robert B. Stoddard.

U.S. Appl. No. 08/878,694, filed Jun. 19, 1997, Lawrence K Pacer.

U.S. Appl. No. 09/270,856, filed Mar. 17, 1999, Gene H. Arts.

U.S. Appl. No. 09/504,640, filed Feb. 16, 2000, James Steven Cunningham.

U.S. Appl. No. 09/666,312, filed Sep. 21, 2000, Robert C. Platt.

U.S. Appl. No. 12/791,100, filed Jun. 1, 2010, Kristin D. Johnson.

U.S. Appl. No. 12/845,842, filed Jul. 29, 2010, Kristin D. Johnson.

Hernandez et al., "A Controlled Study of the Argon Beam Coagultor for Partial Nephrectomy"; The Journal of Urology, vol. 143, May (1990) J. Urol. 143: pp. 1062-1065.

Ward et al., "A Significant New Contribution to Radical Head and Neck Surgery"; Arch Otolaryngology, Head and Neck Surg., vol. 115 pp. 921-923 (Aug. 1989).

Lieberman et al., "Capacitive Discharges", Principles of Plasma Discharges and Materials Processing, John Wiley & Son, Inc. (2005) pp. 387-460.

Moore et al., "Confined Geometry Interactions of Downstream RF-Excited Atmospheric Plasma Wires", IEEE Transactions on Plasma Science, 0093-3813, (2008) pp. 1-2.

Walsh et al., "Contrasting Characteristics of Pulsed and Sinusoidal Cold Atmospheric Plasma Jets", Applied Physics Letters, 88, 171501 (2006) pp. 1-3.

Cho et al. "Coplanar ac Discharges Between Cylindrical Electrodes With a Nanoporous Alumina Dielectric: Modular Dielectric Barrier Plasma Devices", IEEE Transactions on Plasma Science, vol. 33, No. 2, (Apr. 2005) pp. 378-379.

Xu et al., "DBD Plasma Jet in Atmospheric Pressure Argon", IEEE Transactions on Plasma Science, vol. 36, No. 4, (Aug. 2008), pp. 1352-1353.

Alfred Grill, "Electron Cyclotron Resonance Plasmas", Cold Plasma in Materials Fabrication, IEEE Press (1994) pp. 40-43.

Brand et al., "Electrosurgical Debulking of Ovarian Cancer: A New Technique Using the Argon Beam Coagulator"; Gynecologic Oncology 39 pp. 115-118 (1990).

Grund et al., "Endoscopic Argon Plasma . . . Flexible Endoscopy"; Endoscopic Surgery and Allied Technologies, No. 1, vol. 2, pp. 42-46 (Feb. 1994).

Waye et al., "Endoscopic Treatment Options"; Techniques in Therapeutic Endoscopy, pp. 1.7-1.15, (1987).

B.D. Cullity, "Introduction to Magnetic Materials", University of Notre Dame; Addison-Wesley Publishing Company, Reading MA., (1972) pp. 23-28.

Brian Chapman, "Matching Networks", Glow Discharge Processes, John Wiley & Sons Inc., NY, (1980) pp. 153-172.

(56) References Cited

OTHER PUBLICATIONS

Yin et al., "Miniaturization of Inductively Coupled Plasma Sources", IEEE Transactions on Plasma Science, vol. 27, No. 5, (Oct. 1999) pp. 1516-1524.
Park et al., "Nanoporous Anodic Alumina Film on Glass: Improving Transparency by an Ion-Drift Process", Electrochemical and Solid-State Letters, 8 (3) (2005), pp. D5-D7.
P.A. Tulle, "Off-Resonance Microwave-Created Plasmas", Plasma Physics, Pergamon Press (1973) vol. 15, pp. 971-976.
Lieberman et al., "Ohmic Heating", Principles of Plasma Discharges and Materials Processing, John Wiley & Son, Inc. (2005) pp. 97-98.
Lieberman et al., "Optical Actinometry", Principles of Plasma Discharges and Materials Processing, John Wiley & Son, Inc. (2005) pp. 277-279.
Cho et al., "Ozone Production by Nanoporous Dielectric Barrier Glow Discharge in Atmospheric Pressure Air", Applied Physics Letters, 92, 101504, (2008) pp. 1-3.
Lieberman et al., "Particle and Energy Balance in Discharges", Principles of Plasma Discharges and Materials Processing, John Wiley & Son, Inc. (2005) pp. 329-381.
Woloszko et al., "Plasma Characteristics of Repetitively-Pulsed Electrical Discharges in Saline Solutions Used for Surgical Procedures", IEEE Transactions of Plasma Science, vol. 30, No. 3, (Jun. 2002) pp. 1376-1383.
Stoffels et al., "Plasma Needle for In Vivo Medical Treatment: Recent Developments and Perspectives", Plasma Sources Science and Technology 15 (2006) pp. 169-180.
Schaper et al., "Plasma Production and Vapour Layer Production at a Pulse Power Electrode in Saline Solution:", (2008) www.escampig2008.csic.es/PosterSessions/100.
Akitsu et al., "Plasma Sterilization Using Glow Discharge at Atmospheric Pressure", Surface & Coatings Technology 193, (2005) pp. 29-34.
Koo et al., "Room-temperature Slot Microplasma in Atmospheric Pressure Air Between Cylindrical Electrodes With a Nanoporous Alumina Dielectric", Applied Physics Letters, 91, 041502 (2007) pp. 1-3.
Brian Chapman, "Secondary Electron Emission", Glow Discharge Processes, John Wiley & Sons Inc., NY, (1980) pp. 82-138.
Moore et al., "Sensitive, Nonintrusive, In-Situ Measurement of Temporally and Spatially Resolved Plasma Electric Fields", Physical Review Letters, vol. 52, No. 7, (Feb. 13, 1984) pp. 538-541.
Lieberman et al., "Sheaths", Principles of Plasma Discharges and Materials Processing, John Wiley & Son, Inc. (2005) pp. 11-14.
Farin et al., Technology of Argon Plasma . . . Endoscopic Applications; Endoscopic Surgery and Allied Technologies, No. 1, vol. 2, pp. 71-77 (Feb. 1994).
Lieberman et al., "The Collisionless Sheath", Principles of Plasma Discharges and Materials Processing, John Wiley & Son, Inc. (2005) pp. 167-206.
Gupta et al., "The Potential of Pulsed Underwater Streamer Discharges as a Disinfection Technique", IEEE Transactions on Plasma Science, vol. 36, No. 4, (Aug. 2008) pp. 1621-1632.
Mark H. Mellow, "The Role of Endoscopic Laser Therapy in Gastrointestinal Neoplasms"; Advanced Therapeutic Endoscopy, pp. 17-21, (1990).
Silverstein et al., "Thermal Coagulation Therapy for Upper Gastrointestinal Bleeding"; Advanced Therapeutic Endoscopy, pp. 79-84, 1990.
European Search Report EP 01 10 2843.8, dated May 15, 2001.
European Search Report EP 05 00 2257, dated Jun. 1, 2005.
European Search Report EP 05 01 8087, dated Oct. 17, 2005.
European Search Report EP 06 01 9572 dated Nov. 21, 2006.
European Search Report EP 07 00 4356 dated Jul. 2, 2007.
European Search Report EP 07 00 4659 dated Feb. 19, 2008.
European Search Report EP 07 00 4659—partial dated May 24, 2007.
European Search Report EP 09 00 4975 dated Sep. 11, 2009.
European Search Report EP 09 01 0519 dated Nov. 16, 2009.
European Search Report EP 09 01 0520 dated Dec. 10, 2009.
European Search Report EP 09 01 5212.5 dated Apr. 1, 2010.
European Search Report EP 09 17 1599.5 dated Mar. 16, 2010.
European Search Report EP 09 17 1600.1 dated Jan. 26, 2010.
European Search Report EP 10 174107.2 dated Nov. 5, 2010.
European Search Report EP 10 180 912.7 dated Dec. 8, 2010.
European Search Report EP 10 186524.4 dated Feb. 18, 2011.
International Search Report PCT/US98/19284, dated Jan. 14, 1999.
Supplementary European Search Report from Appl. No. EP 09 75 5799 mailed Aug. 31, 2012.
Extended European Search Report issued in Appl. No. 10849146.5 dated Sep. 9, 2013.
A Japanese Office Action, dated Jan. 8, 2014; 6 pages.
Extended European Search Report issued in Appl. No. 10849146.5 dated Sep. 26, 2013; 6 pages.
Extended European Search Report corresponding to European Application No. 09755793.8, dated Jul. 21, 2014; 8 pages.
Japanese Notice of Final Rejection and Denial of Entry of Amendment (with English translation), dated Jun. 2, 2015, corresponding to Japanese Patent Application No. 2013-502548; 15 total pages.
English translation of Japanese Notice of Reasons for Rejection, dated Feb. 18, 2014, corresponding to Japanese Patent Application No. 2013-502548; 6 pages.
English translation of Japanese Notice of Reasons for Rejection, dated Oct. 7, 2014, corresponding to Japanese Patent Application No. 2013-502548; 5 pages.
Australian Patent Examination Report No. 1, dated Apr. 17, 2014, corresponding to Australian Patent Application No. 2010349784; 3 pages.
European Communication dated Jun. 17, 2014, corresponding to European Patent Application No. 10849146.5; 6 pages.
International Search Report, dated Nov. 20, 2009, corresponding to International Patent Applciation No. PCT/US09/05385; 2 pages.
Mark A. Sobolewski, "Current and Voltage Measurements in the Gaseous Electronics Conference RF Reference Cell," Journal of Research of the National Institute of Standards and Technology, vol. 100, No. 4, Jul.-Aug. 1995; pp. 341-351.
International Search Report, dated Dec. 4, 2009, corresponding to International Patent Applciation No. PCT/US09/05389; 2 pages.
International Search Report, dated Apr. 5, 2010, corresponding to International Patent Applciation No. PCT/US09/05398; 2 pages.
International Search Report, dated Nov. 25, 2009, corresponding to International Patent Applciation No. PCT/US09/05389; 2 pages.
European Communication/Examination Report dated Jul. 14, 2015, corresponding to European Patent Application No. 09 845 329.3; 8 pages.

* cited by examiner

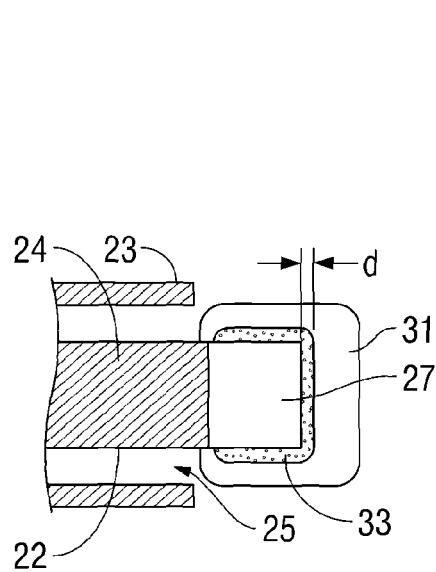
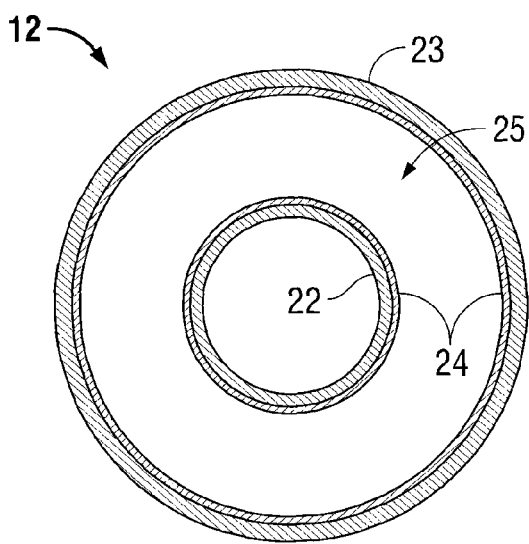
FIG. 3  FIG. 4
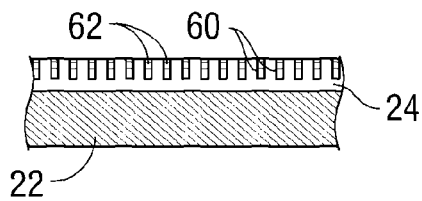
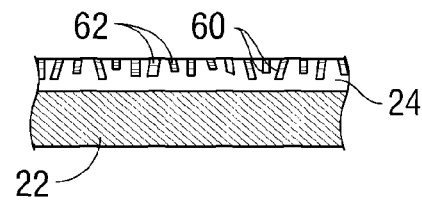
FIG. 5  FIG. 6
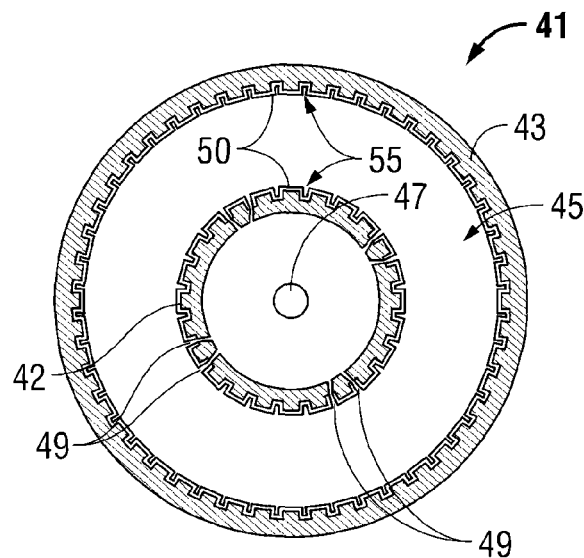
FIG. 7

| $D_T$ AND $L_{R,3}$ AS DESCRIBED IN FIGURE 16 | SECONDARY ELECTRONS IN VOLUME ENHANCE CHEMICAL REACTIONS ($D_T > L_{R,3}$) | SECONDARY ELECTRONS REACH TISSUE SURFACE AND ENHANCE TISSUE SURFACE REACTIONS ($L_{R,3} > D_T > 0$) | ELECTRODE IN CONTACT WITH TISSUE ($I^2R$ HEATING OF BULK TISSUE) CAUSE: ($D_T < 0$) |
|---|---|---|---|
| CHEMICAL EFFECT | YES | YES | MOSTLY BLOCKED |
| HEATING EFFECT | NO | MODERATE | ENHANCED HEATING |
| MIXTURE EFFECT | YES | MODERATE | HEATING DOMINATES |

FIG. 18A

|  | ELECTRODE COATING |
|---|---|
| CHEMICAL EFFECT | INCREASE RADICAL DENSITIES TO ENHANCE TISSUE REACTIONS AT SURFACES |
| HEATING EFFECT | INCREASES RADICAL, SECONDARY AND ELECTRON FLUX TO ENHANCE SURFACE REACTIONS ON TISSUE |

FIG. 18B

| | HEATING EFFECT | CHEMICAL EFFECT | DIRECTIONALITY | SELECTIVITY |
|---|---|---|---|---|
| SHEATH NOT IN CONTACT WITH TISSUE | MINIMAL/NO EFFECT | YES, LIMITED BY LATERAL DIFFUSION LOSS AWAY FROM TISSUE | SOME DUE TO GAS TRANSPORT | YES - CHEMISTRY DOMINATED |
| SHEATH IN CONTACT WITH TISSUE | SMALL/LIMTED EFFECT | STRONG: BOTH CHEMICAL AND ELECTRON FLUX EFFECTS | STRONGEST: BOTH GAS TRANSPORT AND ELECTRON FLUX | STRONG: BOTH CHEMICAL AND ELECTRON FLUX EFFECTS |
| INNER ELECTRODE TOUCHES TISSUE | STRONG EFFECT | SOME BUT REDUCED AT TISSUE-ELECTRODE INTERFACE | SOME | SOME ON SIDES BUT REDUCED AT TISSUE-ELECTRODE INTERFACE |
| INNER ELECTRODES EXTENDS INTO TISSUE | MAXIMUM EFFECT | LIMITED/MINIMAL | ELECTRODE SHAPE DOMINATES | THERMAL EFFECTS DOMINATE, SOME ON SIDES |

FIG. 18C

SYSTEM AND METHODS FOR PLASMA APPLICATION

CROSS-REFERENCE TO RELATED APPLICATION

The present application is a continuation application of U.S. patent application Ser. No. 12/924,404, filed on Sep. 27, 2010, which claims the benefit of and priority to U.S. Provisional Application Ser. No. 61/277,809, filed on Sep. 30, 2009, the entire contents of which are incorporated by reference herein.

U.S. patent application Ser. No. 12/924,404 is also a continuation-in-part application of International Application No. PCT/US2009/045708, filed on May 29, 2009, which claims the benefit of and priority to U.S. Provisional Application Ser. No. 61/057,667, filed on May 30, 2008, the entire contents of which are incorporated by reference herein.

BACKGROUND

1. Technical Field

The present disclosure relates to plasma devices and processes for surface processing and material removal or deposition. More particularly, the disclosure relates to an apparatus and method for generating and directing chemically reactive, plasma-generated species in a plasma device along with excited-state species (e.g., energetic photons) that are specific to the selected ingredients.

2. Background of Related Art

Electrical discharges in dense media, such as liquids and gases at or near atmospheric pressure, can, under appropriate conditions, result in plasma formation. Plasmas have the unique ability to create large amounts of chemical species, such as ions, radicals, electrons, excited-state (e.g., metastable) species, molecular fragments, photons, and the like. The plasma species may be generated in a variety of internal energy states or external kinetic energy distributions by tailoring plasma electron temperature and electron density. In addition, adjusting spatial, temporal and temperature properties of the plasma creates specific changes to the material being irradiated by the plasma species and associated photon fluxes. Plasmas are also capable of generating photons including energetic ultraviolet photons that have sufficient energy to initiate photochemical and photocatalytic reaction paths in biological and other materials that are irradiated by the plasma photons.

SUMMARY

Plasmas have broad applicability to provide alternative solutions to industrial, scientific and medical needs, especially workpiece surface processing at low temperature. Plasmas may be delivered to a workpiece, thereby affecting multiple changes in the properties of materials upon which the plasmas impinge. Plasmas have the unique ability to create large fluxes of radiation (e.g., ultraviolet), ions, photons, electrons and other excited-state (e.g., metastable) species which are suitable for performing material property changes with high spatial, material selectivity, and temporal control. Plasmas may also remove a distinct upper layer of a workpiece but have little or no effect on a separate underlayer of the workpiece or it may be used to selectively remove a particular tissue from a mixed tissue region or selectively remove a tissue with minimal effect to adjacent organs of different tissue type.

One suitable application of the unique chemical species is to drive non-equilibrium or selective chemical reactions at or within the workpiece to provide for selective removal of only certain types of materials. Such selective processes are especially sought in biological tissue processing (e.g., mixed or multi-layered tissue), which allows for cutting and removal of tissue at low temperatures with differential selectivity to underlayers and adjacent tissues. This is particularly useful for removal of biofilms, mixtures of fatty and muscle tissue, debridement of surface layers and removing of epoxy and other non-organic materials during implantation procedures.

The plasma species are capable of modifying the chemical nature of tissue surfaces by breaking chemical bonds, substituting or replacing surface-terminating species (e.g., surface functionalization) through volatilization, gasification or dissolution of surface materials (e.g., etching). With proper techniques, material choices and conditions, one can remove one type of tissue entirely without affecting a nearby different type of tissue. Controlling plasma conditions and parameters (including S-parameters, V, I, $\Theta$, and the like) allows for the selection of a set of specific particles, which, in turn, allows for selection of chemical pathways for material removal or modification as well as selectivity of removal of desired tissue type. The present disclosure provides for a system and method for creating plasma under a broad range of conditions including tailored geometries, various plasma feedstock media, number and location of electrodes and electrical excitation parameters (e.g., voltage, current, phase, frequency, pulse condition, etc.).

The supply of electrical energy that ignites and sustains the plasma discharge is delivered through substantially conductive electrodes that are in contact with the ionizable media and other plasma feedstocks. The present disclosure also provides for methods and apparatus that utilize specific electrode structures that improve and enhance desirable aspects of plasma operation such as higher electron temperature and higher secondary emission. In particular, the present disclosure provides for porous media for controlled release of chemical reactants.

Controlling plasma conditions and parameters allows for selection of a set of specific particles, which, in turn, allows for selection of chemical pathways for material removal or modification as well as selectivity of removal of desired tissue type. The present disclosure also provides for a system and method for generating plasmas that operate at or near atmospheric pressure. The plasmas include electrons that drive reactions at material surfaces in concert with other plasma species. Electrons delivered to the material surface can initiate a variety of processes including bond scission, which enables volatilization in subsequent reactions. The electron-driven reactions act synergistically with associated fluxes to achieve removal rates of material greater than either of the reactions acting alone.

In one embodiment of the present disclosure, a plasma system includes a plasma device, an ionizable media source, and a power source. The plasma device includes an inner electrode and an outer electrode coaxially disposed around the inner electrode. The inner electrode includes a distal portion and an insulative layer that covers at least a portion of the inner electrode. The ionizable media source is coupled to the plasma device and is configured to supply ionizable media thereto. The power source is coupled to the inner and outer electrodes, and is configured to ignite the ionizable media at the plasma device to form a plasma effluent having an electron sheath layer about the exposed distal portion.

The insulative layer may be configured to limit the plasma effluent to the exposed distal portion and to provide a source of secondarily-emitted electrons that form at least a portion of the electron sheath layer. The insulative layer may be formed from a material having a secondary electron emission yield from about 1 to about 10. The inner electrode may be formed from a conductive metal and the insulative layer may be a metallic oxide of the conductive metal.

In another embodiment of the present disclosure, the plasma device further includes an electrode spacer. The electrode spacer is disposed between the inner and outer electrodes. The electrode spacer includes a central opening defined therein and is adapted for insertion of the inner electrode therethrough. The electrode spacer includes at least one flow opening defined therein and is configured to receive the flow of the ionizable media. The at least one flow opening may be disposed radially around the central opening.

In another embodiment of the present disclosure, a plasma device includes outer and inner electrodes. The plasma device is configured to receive ionizable media. The outer electrode has a substantially cylindrical tubular shape. The inner electrode is coaxially disposed within the outer electrode. The inner electrode includes a distal portion and an insulative layer. The insulative layer covers at least a portion of the inner electrode. The insulative layer is configured to limit the plasma effluent to the exposed distal portion and provide a source of secondarily-emitted electrons to form an electron sheath layer about the exposed distal portion. The insulative layer may be from a material having a secondary electron emission yield from about 1 to about 10. The inner conductor may be formed from a conductive metal and the insulative layer may be a metallic oxide of the conductive metal.

The plasma device may further include an electrode spacer. The electrode spacer is disposed between the inner and outer electrodes. The electrode spacer may include at least one flow opening defined therein and is configured to receive the flow of the ionizable media. The at least one flow opening may be disposed radially around the central opening.

In yet another embodiment of the present disclosure, a plasma system includes inner and outer electrodes, an ionizable media source, and a power source. The outer electrode has a substantially cylindrical tubular shape. The inner electrode is coaxially disposed within the outer electrode. The inner electrode includes a distal portion and an insulative layer that covers at least a portion of the inner electrode. The insulative layer is configured to limit the plasma effluent to the exposed distal portion and provides a source of secondarily-emitted electrons. The ionizable media source is coupled to the plasma device and is configured to supply ionizable media thereto. The power source is coupled to the inner and outer electrodes, and is configured to ignite the ionizable media at the plasma device to form a plasma effluent having an electron sheath layer of a predetermined thickness formed from the secondarily-emitted electrons. The electron sheath layer is formed about the exposed distal portion.

The insulative layer may be formed from a material having a secondary electron emission yield from about 1 to about 10. The inner conductor may be formed from a conductive metal and the insulative layer may be a metallic oxide of the conductive metal. The plasma device may further include an electrode spacer disposed between the inner and outer electrodes. The electrode spacer may include a central opening defined therein and may be adapted for insertion of the inner electrode therethrough. The electrode spacer may include at least one flow opening defined therein and may be configured for the flow of the ionizable media. The at least one flow opening may be disposed radially around the central opening. The predetermined thickness of the electron sheath layer may be adjustable by selecting a specific ionizable media having a predetermined media density and an average particle cross-section. The predetermined thickness of the electron sheath layer may be inversely proportional to the media density of the ionizable media and the average particle cross-section.

In one embodiment of the present disclosure, a plasma system includes a plasma device, an ionizable media source, and a power source. The plasma device includes an inner electrode and an outer electrode coaxially disposed around the inner electrode. At least one of the inner electrode and the outer electrode is formed from a metal alloy and includes a dielectric coating covering at least a portion thereof. The ionizable media source is coupled to the plasma device and is configured to supply ionizable media thereto. The power source is coupled to the inner and outer electrodes and is configured to ignite the ionizable media at the plasma device to form a plasma effluent.

The dielectric coating may be selected from the group consisting of an oxide, a nitride, a native oxide and a native nitride. The metal alloy may be selected from the group consisting of an aluminum alloy and a titanium alloy. At least one of the inner electrode and the outer electrode may include a plurality of grooves disposed on an outer surface and an inner surface, respectively. The plurality of grooves may be arranged in parallel with a longitudinal axis of at least one of the inner electrode and the outer electrode. The plurality of grooves may be arranged in a spiral configuration. The coating may include a plurality of nanostructure pores. The plurality of pores may include at least one precursor feedstock disposed therein.

In yet another embodiment of the present disclosure, a plasma device configured to receive ionizable media includes outer and inner electrodes. The outer electrode has a substantially cylindrical tubular shape. The inner electrode is coaxially disposed within the outer electrode. At least one of the inner electrode and the outer electrode is formed from a metal alloy and includes a coating formed from a native oxide or a native nitride covering at least a portion thereof. The metal alloy may be selected from the group consisting of an aluminum alloy and a titanium alloy. At least one of the inner electrode and the outer electrode may include a plurality of grooves disposed on an outer surface and an inner surface, respectively. The plurality of grooves may be arranged in at least one of a spiral configuration or in parallel with a longitudinal axis of at least one of the inner electrode and the outer electrode. The coating may include a plurality of nanostructure pores. The plurality of pores may include at least one precursor feedstock disposed therein.

In yet another embodiment of the present disclosure, a plasma system includes a plasma device including outer and inner electrodes. The outer electrode has a substantially cylindrical tubular shape. The outer electrode is formed from a metal alloy and includes a dielectric coating disposed on an inner surface thereof configured to provide a first source of secondarily-emitted electrons. The inner electrode is coaxially disposed within the outer electrode. The inner electrode is formed from a metal alloy and includes a dielectric coating disposed on an outer surface thereof configured to provide a second source of secondarily-emitted electrons. The ionizable media source is coupled to the plasma device and is configured to supply ionizable media thereto. The power source is coupled to the inner and outer electrodes, and is configured to ignite the ionizable media at the plasma device to form a plasma effluent having a first electron sheath layer of a predetermined thickness formed from the first source of secondarily-emitted electrons and a second electron sheath layer of a predetermined thickness formed from the second source of secondarily-emitted electrons.

The metal alloy may be selected from the group consisting of an aluminum alloy and a titanium alloy. The dielectric coating may be selected from the group consisting of an oxide, a nitride, a native oxide and a native nitride. At least one of the inner electrode and the outer electrode may include a plurality of grooves disposed on an outer surface and an inner surface, respectively. The plurality of grooves may be arranged in at least one of a spiral configuration or in parallel with a longitudinal axis of at least one of the inner electrode and the outer electrode. The coating may include a plurality of nanostructure pores having at least one precursor feedstock disposed therein. The first and second electron sheath layers may overlap to produce a hollow cathode effect. At least one of the dielectric coating of the outer electrode, the dielectric coating of the inner electrode, and the power source may be adapted to adjust the thickness of the first and second electron sheath layers such that the first and second electron sheath layers overlap to produce a hollow cathode effect.

In an embodiment of the present disclosure, a plasma device includes inner and outer electrodes. The inner electrode has a substantially cylindrical tubular shape and an opening defined therethrough. The inner electrode has a proximal portion. The outer electrode has a substantially cylindrical tubular shape. The outer electrode is coaxially disposed about the proximal portion of the inner electrode. The dielectric spacer includes a substantially toroidal shape disposed between the inner and the outer electrode. The inner and outer electrodes are configured to couple to an ionizable media source configured to supply ionizable media thereto. The inner and outer electrodes are configured to couple to a power source configured to ignite the ionizable media at the plasma device to form a plasma effluent.

The plasma device may further include a porous member. The porous member is coupled to the inner electrode at a distal end thereof. The porous member is formed from a conductive porous material and is configured to disperse the plasma effluent through the conductive porous material to generate a wide-area plasma effluent. The outer electrode may be disposed only about a portion of the inner electrode.

In yet another embodiment of the present disclosure, a plasma device configured to receive ionizable media includes a dielectric housing, and first and second electrodes. The dielectric housing has a substantially cylindrical tubular shape and an opening defined therethrough. The first and second electrodes are disposed within the opening of the dielectric housing separated by a predetermined distance. The second electrode is formed from a conductive porous material and is configured to ignite the ionizable media to form a plasma having a wide-area plasma effluent.

The first electrode may be a substantially cylindrical rod formed from a conductive metal and disposed coaxially within the dielectric housing. The plasma device may further include an electrode spacer disposed between the first and second electrodes. The electrode spacer is configured to secure the first electrode to the dielectric housing. The electrode spacer includes a central opening adapted for insertion of the first electrode therethrough. The electrode spacer may include at least one flow opening for the flow of the ionizable media disposed radially around the central opening. The first electrode includes an insulative layer that covers at least a portion thereof. The insulative layer may be at least one of formed integrally with the dielectric housing and formed from a dielectric coating deposited on the first electrode. The first electrode may be formed from a conductive porous material. The plasma device may include a dielectric spacer disposed between the first and second electrodes. The dielectric spacer may be formed from a porous dielectric material.

In yet another embodiment of the present disclosure, a plasma device includes a dielectric spacer, and first and second electrodes. The dielectric spacer includes a substantially disk-like shape and is configured to couple to an ionizable media source configured to supply ionizable media thereto. The dielectric spacer is formed from a porous dielectric material configured to disperse the ionizable media. The first and second electrodes are disposed within the dielectric spacer. The first and second electrodes are configured to couple to a power source configured to ignite the ionizable media at the plasma device to form a plasma effluent. The dielectric spacer may include at least one opening to provide for a flow path of the ionizable media through the dielectric spacer. The first and second electrodes may be substantially cylindrical rods formed from a conductive metal and disposed in a parallel configuration with respect to each other and equidistant from a center of the dielectric spacer.

In an embodiment of the present disclosure, a method of treating tissue includes: positioning a plasma device in spaced relation to target tissue in accordance with a target tissue effect; and generating plasma including secondarily-emitted electrons sufficient such that the target tissue effect is achieved. The plasma device may include an inner electrode and an outer electrode coaxially disposed around the inner electrode. The inner electrode may include a distal portion and an insulative layer that covers at least a portion of one of the inner electrode and an inner surface of outer electrode. The secondarily-emitted electrons may have an electron voltage from about 2 eV to about 10 eV, and the secondarily-emitted electrons may have a secondary electron emission yield from about 1 to about 10.

The method may further include generating an electron sheath adjacent to a portion of an electrode of the plasma device. The step of positioning may further comprise selecting the target tissue effect from among a plurality of tissue effects, e.g., the plurality of tissue effects may include a chemical effect, a heating effect, and a mixture effect. The step of positioning may further comprise: determining a first distance between an electrode of the plasma device and the target tissue in accordance with the target tissue effect; and positioning the electrode about the first distance from the tissue. The step of positioning may include contacting an electrode of the plasma device with the target tissue.

The electrode of the plasma device has a working range having energetic secondary electron emissions and the step of positioning may include positioning a distal end of the electrode such that a distance between the distal end and the target tissue is greater than the working range and/or positioning a distal end of the electrode such that a distance between the distal end and the target tissue is less than the working range.

The method may further include one or more of: selecting a target working range of an electrode of the plasma device, the target working range having energetic secondary electron emissions; supplying power to the electrode as a function of the selected target working range; selecting a target electron sheath of an electrode of the plasma device; and supplying power to the electrode such that the electrode generates an electron sheath about equal to the target electron sheath.

In an embodiment of the present disclosure, a method of treating tissue includes: selecting a first target magnitude of a heating effect for target tissue; selecting a second target magnitude of a chemical effect for the target tissue; positioning a plasma device having at least one electrode in spaced relation to the target tissue in accordance with the first and second target magnitudes; and generating plasma including secondarily-emitted electrons sufficient for the first and second target magnitudes. The step of positioning may include one or more of: determining a first distance between the at least one electrode and the target tissue in accordance with the selected first and second target magnitudes; positioning the at least one electrode about the first distance from the tissue; and/or contacting the at least one electrode with tissue. The method may further include: selecting a target working range of the at least one electrode, the target working range having energetic secondary electron emissions; and supplying power to the at least one electrode as a function of the selected target working range.

In another embodiment of the present disclosure, a method of treating tissue includes: selecting one of a target directivity and a target selectivity; positioning a plasma device having at least one electrode in spaced relation to tissue in accordance with the selected one of the target directivity and the target selectivity; and generating plasma including secondarily-emitted electrons sufficient for the selected one of the target directivity and the target selectivity. The step of selecting may include one or more of: selecting a first target magnitude of a heating effect on tissue; and selecting a second target magnitude of a chemical effect on tissue. The step of positioning may further include positioning the plasma device in spaced relation to tissue in accordance with the first and second target magnitudes. The step of positioning may include: determining a first distance between the at least one electrode and tissue in accordance with the selected one of the target directivity and the target selectivity; and/or positioning the at least one electrode about the first distance from the tissue.

BRIEF DESCRIPTION OF THE DRAWINGS

FIG. 3 is a side, cross-sectional view of the plasma device of FIG. 2A;

FIG. 4 is a front, cross-sectional view of the plasma device of FIG. 2A according to the present disclosure;

FIG. 5 is an enlarged cross-sectional view of a plasma device according to the present disclosure;

FIG. 6 is an enlarged cross-sectional view of a plasma device according to one embodiment of the present disclosure;

FIG. 7 is a front, cross-sectional view of the plasma device of FIG. 2A according to the present disclosure;

FIGS. 18A, 18B, and 18C show charts illustrating several tissue effects of a plasma device according to the present disclosure;

DETAILED DESCRIPTION

Plasmas are generated using electrical energy that is delivered as either direct current (DC) electricity or alternating current (AC) electricity at frequencies from about 0.1 hertz (Hz) to about 100 gigahertz (GHz), including radio frequency ("RF", from about 0.1 MHz to about 100 MHz) and microwave ("MW", from about 0.1 GHz to about 100 GHz) bands, using appropriate generators, electrodes, and antennas. Choice of excitation frequency, the workpiece, as well as the electrical circuit that is used to deliver electrical energy to the circuit affects many properties and requirements of the plasma. The performance of the plasma chemical generation, the delivery system and the design of the electrical excitation circuitry are interrelated—as the choices of operating voltage, frequency and current levels (as well as phase) effect the electron temperature and electron density. Further, choices of electrical excitation and plasma device hardware also determine how a given plasma system responds dynamically to the introduction of new ingredients to the host plasma gas or liquid media. The corresponding dynamic adjustment of the electrical drive, such as via dynamic match networks or adjustments to voltage, current, or excitation frequency may be used to maintain controlled power transfer from the electrical circuit to the plasma.

Figure 1:
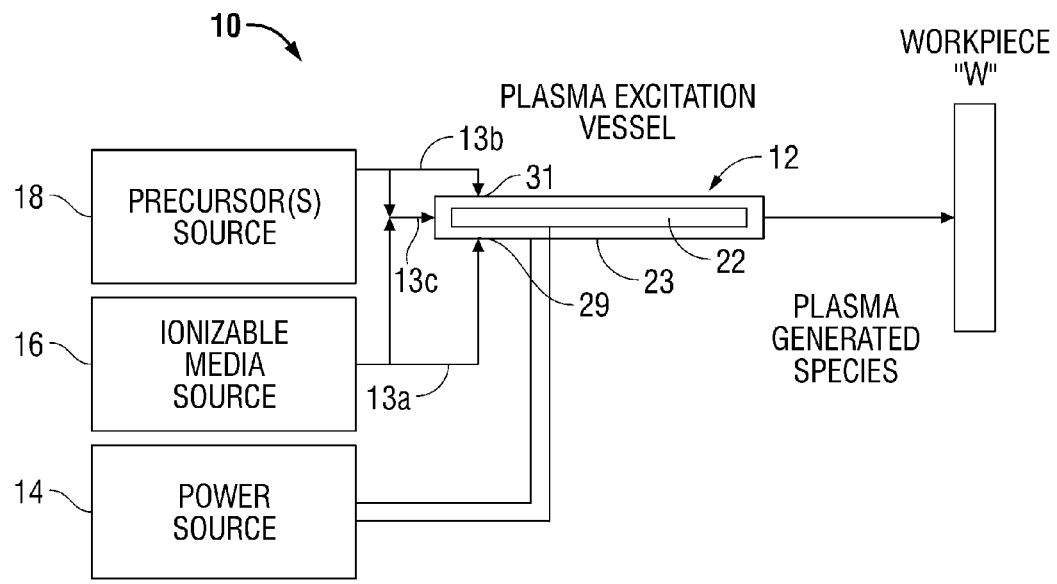
FIG. 1 is a schematic diagram of a plasma system according to the present disclosure.

Referring initially to FIG. 1, a plasma system 10 is disclosed. The system 10 includes a plasma device 12 that is coupled to a power source 14, an ionizable media source 16 and a precursor source 18. Power source 14 includes any suitable components for delivering power or matching impedance to plasma device 12. More particularly, the power source 14 may be any radio frequency generator or other suitable power source capable of producing power to ignite the ionizable media to generate plasma. The plasma device 12 may be utilized as an electrosurgical pencil for application of plasma to tissue and the power source 14 may be an electrosurgical generator that is adapted to supply the device 12 with electrical power at a frequency from about 0.1 MHz to about 2,450 MHz and in another embodiment from about 1 MHz to about 13.56 MHz. The plasma may also be ignited by using continuous or pulsed direct current (DC) electrical energy.

The precursor source 18 may be a bubbler or a nebulizer configured to aerosolize precursor feedstocks prior to introduction thereof into the device 12. The precursor source 18 may also be a micro droplet or injector system capable of generating predetermined refined droplet volume of the precursor feedstock from about 1 femtoliter to about 1 nanoliter in volume. The precursor source 18 may also include a microfluidic device, a piezoelectric pump, or an ultrasonic vaporizer.

The system 10 provides a flow of plasma through the device 12 to a workpiece "W" (e.g., tissue). Plasma feedstocks, which include ionizable media and precursor feedstocks, are supplied by the ionizable media source 16 and the precursor source 18, respectively, to the plasma device 12. During operation, the precursor feedstock and the ionizable media are provided to the plasma device 12 where the plasma feedstocks are ignited to form plasma effluent containing ions, radicals, photons from the specific excited species and metastables that carry internal energy to drive desired chemical reactions in the workpiece "W" or at the surface thereof. The feedstocks may be mixed upstream from the ignition point or midstream thereof (e.g., at the ignition point) of the plasma effluent, as shown in FIG. 1 and described in more detail below.

The ionizable media source 16 provides ionizable feedstock to the plasma device 12. The ionizable media source 16 is coupled to the plasma device 12 and may include a storage tank and a pump (not explicitly shown). The ionizable media may be a liquid or a gas such as argon, helium, neon, krypton, xenon, radon, carbon dioxide, nitrogen, hydrogen, oxygen, etc. and their mixtures, and the like, or a liquid. These and other gases may be initially in a liquid form that is gasified during application.

The precursor source 18 provides precursor feedstock to the plasma device 12. The precursor feedstock may be either in solid, gaseous or liquid form and may be mixed with the ionizable media in any state, such as solid, liquid (e.g., particulates or droplets), gas, and the combination thereof. The precursor source 18 may include a heater, such that if the precursor feedstock is liquid, it may be heated into gaseous state prior to mixing with the ionizable media.

In one embodiment, the precursors may be any chemical species capable of forming reactive species such as ions, electrons, excited-state (e.g., metastable) species, molecular fragments (e.g., radicals) and the like, when ignited by electrical energy from the power source 14 or when undergoing collisions with particles (electrons, photons, or other energy-bearing species of limited and selective chemical reactivity) formed from ionizable media 16. More specifically, the precursors may include various reactive functional groups, such as acyl halide, alcohol, aldehyde, alkane, alkene, amide, amine, butyl, carboxlic, cyanate, isocyanate, ester, ether, ethyl, halide, haloalkane, hydroxyl, ketone, methyl, nitrate, nitro, nitrile, nitrite, nitroso, peroxide, hydroperoxide, oxygen, hydrogen, nitrogen, and combination thereof. In embodiments, the chemical precursors may be water, halogenoalkanes, such as dichloromethane, tricholoromethane, carbon tetrachloride, difluoromethane, trifluoromethane, carbon tetrafluoride, and the like; peroxides, such as hydrogen peroxide, acetone peroxide, benzoyl peroxide, and the like; alcohols, such as methanol, ethanol, isopropanol, ethylene glycol, propylene glycol, alkalines such as NaOH, KOH, amines, alkyls, alkenes, and the like. Such chemical precursors may be applied in substantially pure, mixed, or soluble form.

The precursors and their functional groups may be delivered to a surface to react with the surface species (e.g., molecules) of the workpiece "W." In other words, the functional groups may be used to modify or replace existing surface terminations of the workpiece "W." The functional groups react readily with the surface species due to their high reactivity and the reactivity imparted thereto by the plasma. In addition, the functional groups are also reacted within the plasma volume prior to delivering the plasma volume to the workpiece.

Some functional groups generated in the plasma can be reacted in situ to synthesize materials that subsequently form a deposition upon the surface. This deposition may be used for stimulating healing, killing bacteria, and increasing hydrophilic or hydroscopic properties. In addition, deposition of certain function groups may also allow for encapsulation of the surface to achieve predetermined gas/liquid diffusion, e.g., allowing gas permeation but preventing liquid exchange, to bond or stimulate bonding of surfaces, or as a physically protective layer.

The precursor source 18 and the ionizable media source 16 may be coupled to the plasma device 12 via tubing 13a and 13b, respectively. The tubing 13a and 13b may be combined into tubing 13c to deliver a mixture of the ionizable media and the precursor feedstock to the device 12 at a proximal end thereof. This allows for the plasma feedstocks, e.g., the precursor feedstock and the ionizable gas, to be delivered to the plasma device 12 simultaneously prior to ignition of the mixture therein.

In another embodiment, the ionizable media source 16 and the precursors source 18 may be coupled to the plasma device 12 via the tubing 13a and 13b at separate connections, e.g., the first connection 31 and a second connection 29, respectively, such that the mixing of the feedstocks occurs within the plasma device 12 upstream from the ignition point. In other words, the plasma feedstocks are mixed proximally of the ignition point, which may be any point between the respective sources 16 and 18 and the plasma device 12, prior to ignition of the plasma feedstocks to create the desired mix of the plasma effluent species for each specific surface treatment on the workpiece "W."

In a further embodiment, the plasma feedstocks may be mixed midstream, e.g., at the ignition point or downstream of the plasma effluent, directly into the plasma. More specifically, the first and second connections 31, 29 may be coupled to the device 12 at the ignition point, such that the precursor feedstocks and the ionizable media are ignited concurrently as they are mixed (FIG. 1). It is also envisioned that the ionizable media may be supplied to the device 12 proximally of the ignition point, while the precursor feedstocks are mixed therewith at the ignition point.

In a further illustrative embodiment, the ionizable media may be ignited in an unmixed state and the precursors may be mixed directly into the ignited plasma. Prior to mixing, the plasma feedstocks may be ignited individually. The plasma feedstock is supplied at a predetermined pressure to create a flow of the medium through the device 12, which aids in the reaction of the plasma feedstocks and produces a plasma effluent. The plasma according to the present disclosure is generated at or near atmospheric pressure under normal atmospheric conditions.

Figure 2A:
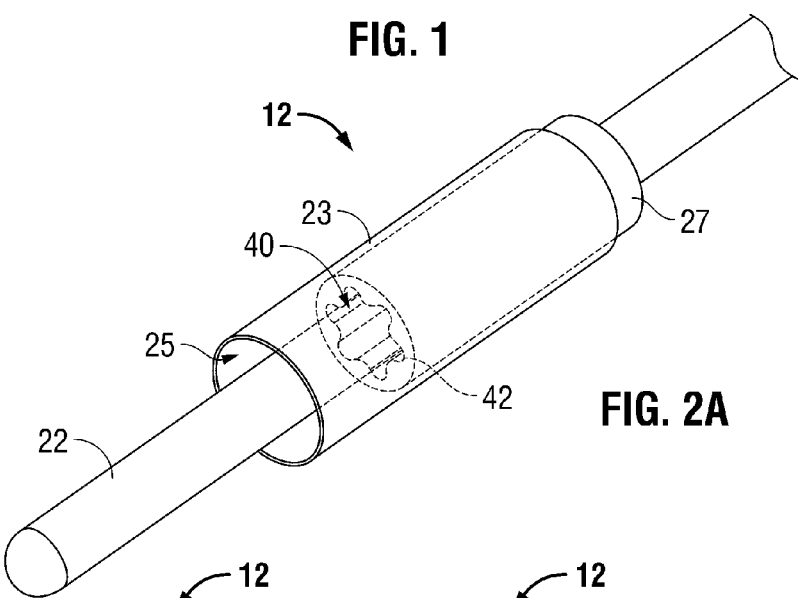
FIG. 2A is a perspective, cross-sectional view of a plasma device according to the present disclosure.

With reference to FIGS. 1-3, the device 12 includes an inner electrode 22 disposed coaxially within an outer electrode 23. As shown in FIG. 2A, the outer electrode 23 has a substantially cylindrical tubular shape having an opening 25 (FIG. 3) defined therein. The inner electrode 22 has a substantially cylindrical shape (e.g., rod-shaped). The electrodes 22 and 23 may be formed from a conductive material suitable for ignition of plasma such as metals and metal-ceramic composites. In one embodiment, the electrodes 22 and 23 may be formed from a conductive metal including a native oxide or nitride compound disposed thereon.

The device 12 also includes an electrode spacer 27 disposed between the inner and outer electrodes 22 and 23. The electrode spacer 27 may be disposed at any point between the inner and outer electrodes 22 and 23 to provide for a coaxial configuration between the inner and outer electrodes 22 and 23. The electrode spacer 27 includes a central opening 40 adapted for insertion of the inner electrode 22 therethrough and one or more flow openings 42 disposed radially around the central opening 40 to allow for the flow of ionizable media and precursors through the device 12. The electrode spacer 27 may be frictionally fitted to the electrodes 22 and 23 to secure the inner electrode 22 within the outer electrode 23. In another embodiment, the electrode spacer 27 is slidably disposed over the inner electrode 22. In one illustrative embodiment, the electrode spacer 27 may be formed from a dielectric material, such as ceramic, to provide capacitive coupling between the inner and outer electrodes 22 and 23.

Figures 2B, 2C, 2D:
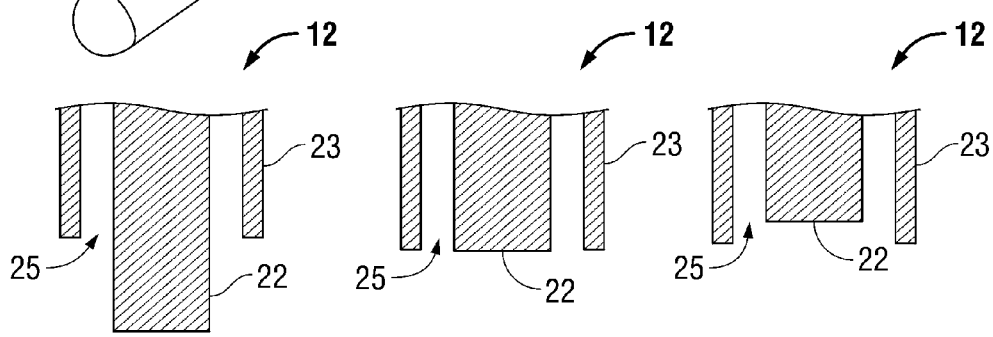
FIGS. 2B-2D are side, cross-sectional views of the plasma device of FIG. 2A.

As shown in FIG. 2B, distal end of the inner electrode 22 may extend past the distal end of the outer electrode 23. In another embodiment, as shown in FIGS. 2C and 2D, the inner electrode 22 may be fully enclosed by the outer electrode 23. In particular, the distal end the inner electrode 22 may be flush with the distal end of the outer electrode 23 (FIG. 2C). In a further embodiment, the inner electrode 22 may be recessed within the outer electrode 23 (e.g., distal end of the inner electrode 22 is within the opening 25 as shown in FIG. 2D).

The extended distance of the inner electrode 22 relative to the outer electrode 23 may be adjusted to achieve a desired spatial relationship between the electrodes 22 and 23. In one embodiment, the electrode spacer 27 is secured to the outer electrode 23 but is slidably disposed over the inner electrode 22. In other words, the inner electrode 22 may move through the opening 40. This allows for the outer electrode 23 and the electrode spacer 27 to be longitudinally movable along the inner electrode 22 thereby controlling the exposure of the distal end of the inner electrode 22. In another embodiment, the inner and outer electrodes 22 and 23 may be fixated in a coaxial configuration using other fixation mechanisms (e.g., clamps) that allow for adjustment of the exposure distance of the inner electrode 22.

One of the electrodes 22 and 23 may be an active electrode and the other may be a neutral or return electrode to facilitate in RF energy coupling. Each of the electrodes 22 and 23 are coupled to the power source 14 that drives plasma generation and electron sheath formation close to the inner electrode 22, such that the energy from the power source 14 may be used to ignite the plasma feedstocks flowing through the device 12. More specifically, the ionizable media and the precursors flow through the device 12 through the opening 25 (e.g., through the electrode spacer 27 and between the inner and outer electrodes 22 and 23). The inner electrode 22 may also include one or more openings (not explicitly shown) therethrough to facilitate the flow of ionizable media and the precursors. When the electrodes 22 and 23 are energized, the plasma feedstocks are ignited and form a plasma effluent which is emitted from the distal end of the device 12 onto the workpiece "W."

As shown in FIG. 3, the inner electrode 22 includes a coating 24 that covers at least a portion of the inner electrode 22 leaving an exposed (e.g., uninsulated or uncoated) distal portion 27 of the inner electrode 22 uninsulated. In another embodiment, the coating 24 may be disposed on the outer electrode 23 as discussed in more detail below with respect to FIGS. 4-7 and 16.

The coating 24 may be formed from an insulative or semi-conductive material deposited as a film onto the inner conductor (e.g., atomic layer deposition) or as a dielectric sleeve or layer. In one illustrative embodiment, the insulative cover 24 may be a native metal oxide. The coating 24 limits the plasma action to the distal portion 27 and provides for the creation of a plasma effluent 31 having an energetic electron sheath layer 33. The sheath layer 33 has a reaching distance "d" from about 1 to about 10 mm, suitable for contacting the sheath layer 33 to the workpiece "W" to promote volatilization and/or modification of chemical bonds at the surface thereof as discussed in more detail below with respect to FIGS. 16-24.

In addition, the coating 24 provides for capacitive coupling between the inner and outer electrodes 22 and 23. The resulting capacitive circuit element structure provides for a net negative bias potential at the surface of the inner electrode 22, which attracts the ions and other species from the plasma effluent. These species then bombard the coating 24 and release the electrons generating the sheath layer 33.

The sheath layer 33 is generated in part by the materials of the electrodes 22 and 23 and in particular by the coating 24. Materials having high secondary electron emission property, γ, in response to ion and/or photon bombardment are suitable for this task. Such materials include insulators and/or semiconductors. These materials have a relatively high γ, where γ represents the number of electrons emitted per incident bombardment particle. Thus, metals generally have a low γ (e.g., less than 0.1) while insulative and semiconductor materials, such as metallic oxides have a high γ, from about 1 to about 10 with some insulators exceeding a value of 20. Thus, the coating 24 acts as a source of secondary emitted electrons, in addition to limiting the plasma to the distal end of the inner electrode 22.

Secondary electron emission, γ, may be described by the formula (1):

$$\gamma = \Gamma_{secondary}/\Gamma_{ion} \qquad (1)$$

In formula (1) γ is the secondary electron emission yield or coefficient, $\Gamma_{secondary}$ is the electron flux, and $\Gamma_{ion}$ is the ion flux. Secondary emission occurs due to the impacts of plasma species (ions) onto the coating 24 when the ion impact collisions have sufficient energy to induce secondary electron emission, thus generating γ-mode discharges. Generally discharges are said to be in γ-mode when electron generation occurs preferentially at electrode surfaces (i.e., γ>1) instead of in the gas (an α-mode discharge). In other words, per each ion colliding with the coating 24, a predetermined number of secondary electrons are emitted. Thus, γ may also be thought of as a ratio of the $\Gamma_{secondary}$ (e.g., the electron flux) and $\Gamma_{ion}$ (e.g., the ion flux).

These ion collisions with the surface of the coating 24, in turn, provide sufficient energy for secondary electron emission to generate γ discharges. The ability of coating materials such as coating 24 to generate γ discharges varies with several parameters, with the most influence due to the choice of materials having a high γ as discussed above. This property allows coatings 24 to act as a source of secondary emitted electrons or as a catalytic material to enhance selected chemical reaction paths.

Over time the coating 24 may thin or be removed during the plasma operation. In order to maintain the coating 24 to continually provide a source of secondary emitted electrons, the coating 24 may be continually replenished during the plasma operation. This may be accomplished by adding species that reformulate the native coating 24 on the inner and outer electrodes 22 and 23. In one embodiment, the precursor source 18 may provide either oxygen or nitrogen gas to the device 12 to replenish to oxide or nitride coating.

Generation of the sheath layer 33 is also controlled by the supply of the ionizable media and the precursors. Ionizable media and the precursors are selected that are relatively transparent to the energetic electrons released during secondary emission from the surface of the inner electrode 22. As stated above, the plasma is generated at atmospheric pressure. Due to the increased entropy at such pressure, the generated electrons undergo a multitude of collisions in a relatively short period of time and space forming the sheath layer 33.

The thickness of the sheath layer 33 is defined by a formula (2):

$$\text{Thickness}=1/N\sigma \quad (2)$$

In formula (2), N is the number of scattering centers, which may be the molecules of the ionizable media, the precursors and the atmospheric gases. Thus, N defines the media density. The variable, σ, is the average particle cross-section of the scattering centers. The thickness of the sheath layer 33 is inversely proportional to the product of N and σ. Thus, decreasing N and σ allows for achieving a thicker sheath layer 33. A lower σ may be provided by using specific ionizable media compounds with molecules having a low cross-section, such as hydrogen and helium. The variable N may be lowered by heating the ionizable media to reduce the gas density and limiting the amount of media provided to the lowest amount needed to sustain the plasma reaction.

The present disclosure also relates to systems and methods for generating plasma effluents having the energetic electron sheath layer having a reaching distance "d." The sheath layer 33 is produced by the combination of disclosed electrode structures, specific gas species, electrode materials, proper excitation conditions, and other media parameters. The propagation of energetic electron for mm-sized distances provides for practical applications on a variety of surfaces, such as modification of chemical bonds on the surface and volatilization of surface compounds.

In another embodiment as shown in FIGS. 4-6, the coating 24 is disposed on the outer surface of the inner electrode 22 and on the inner surface of the outer electrode 23. In other words, the surfaces of the inner and outer electrodes 22 and 23 facing the opening 25 include the coating 24. In one embodiment, the coating 24 may cover the entire surface of the inner and outer electrodes 22 and 23 (e.g., outer and inner surface thereof, respectively). In another embodiment, the coating 24 may cover only a portion of the electrodes 22 and 23, such as a distal, proximal (e.g., FIG. 3 illustrates an uncoated distal portion 27) or middle portions thereof.

The coating 24 may be a native oxide, or a native nitride of the metal from which the inner and outer electrodes are formed, or may be a deposited layer or a layer formed by ion implantation. In one illustrative embodiment, the inner and outer electrodes 22 and 23 are formed from an aluminum alloy and the coating 24 is aluminum oxide ($Al_2O_3$) or aluminum nitride (AlN). In another illustrative embodiment, the inner and outer electrodes 22 and 23 are formed from a titanium alloy and the coating 24 is titanium oxide ($TiO_2$) or titanium nitride (TiN).

The inner and outer electrodes 22 and 23 and the coating 24 may also be configured as a heterogeneous system. The inner and outer electrodes 22 and 23 may be formed from any suitable electrode substrate material (e.g., conductive metal or a semiconductor) and the coating 24 may be disposed thereon by various coating processes. The coating 24 may be formed on the inner and outer electrodes 22 and 23 by exposure to an oxidizing environment, anodization, electrochemical processing, ion implantation, or deposition (e.g., sputtering, chemical vapor deposition, atomic layer deposition, etc.).

In another embodiment the coating 24 on electrodes 22 and 23 may be different on each electrode and may serve separate purposes. One coating 24 (e.g., on the electrode 22) can be selected to promote increased secondary electron emission while coating 24 on the other electrode (e.g., electrode 23) can be selected to promote specific chemical reactions (e.g., act as a catalyst).

As shown in FIGS. 5 and 6, the coating 24 may also include a plurality of nanostructure pores 60, which may be arranged in a predetermined (e.g., unidirectional) form (FIG. 5) or in a random configuration (FIG. 6). Pores 60 may be formed during the coating processes discussed above. In one illustrative embodiment, the pores 60 may be treated to include one or more types of precursor feedstock 62 disposed therein. This allows for feeding of the precursor feedstock 62 directly into the plasma effluent either as a substitute for the precursor source 18 or in conjunction therewith. The precursor feedstock 62 may be the precursors discussed above with respect to the precursor source 18. In one embodiment, the precursor feedstock 62 may be a catalyst suitable for initiation of the chemical reactions between the precursor feedstock supplied from the precursor source 18 and the plasma.

FIG. 7 shows a side cross-sectional view of a plasma device 41 having an inner electrode 42 disposed coaxially within an outer electrode 43. The outer electrode 43 has a substantially cylindrical tubular shape having an opening 45 defined therein. The inner electrode 42 has a substantially cylindrical shape and may be fully enclosed by the outer electrode 43 or extend past the distal end of the outer electrode 43.

The device 41 also includes an electrode spacer (not explicitly shown) disposed between the inner and outer electrodes 42 and 43, similar to the electrode spacer 27. The electrode spacer may be disposed at any point between the inner and outer electrodes 42 and 43 to provide for a coaxial configuration between the inner and outer electrodes 42 and 43. The electrode spacer may be frictionally fitted to the electrodes 42 and 43 to secure the inner electrode 42 within the outer electrode 43. In one illustrative embodiment, the electrode spacer may be formed from a dielectric material, such as ceramic, to provide for capacitive coupling between the inner and outer electrodes 42 and 43.

Each of the inner and outer electrodes 42 and 43 may include a plurality of geometrical arrangements. In one embodiment, as shown in FIG. 7, the inner and outer electrodes 42 and 43 include a plurality of grooves 55 disposed on the surface thereof. The grooves 55 enhance the local electrical fields along the inner and outer electrodes 42 and 43. The grooves 55 may also be covered by a groove coating 50, which is substantially similar to the coating 24 for similar functional purposes. The grooves 55 are disposed on the outer surface of the inner electrode 42 and on the inner surface of the outer electrode 43. The inner and outer electrodes 42 and 43 and the coating 50 may be formed from the materials discussed above with respect to the inner and outer electrodes 22 and 23. In one embodiment, the groove coating 50 may be formed from substantially similar materials as the coating 24, namely, a combination of aluminum, magnesium, or titanium metals, and oxides or nitrides thereof.

The grooves 55 may be arranged in parallel with a longitudinal axis defined by the inner and outer electrodes 42 and 43. In another embodiment, the grooves 45 may be arranged in a spiral configuration (e.g., rifled) on the inner and outer electrodes 42 and 43. The inner electrode 43 may also include one or more side vents 49 to allow for additional gas flow into the opening 45.

The present disclosure provides for a variety of plasma device embodiments and configurations suitable for wide area plasma treatment of tissue. Common to the disclosed embodiments is the uniform dispersion of plasma feedstocks in the vicinity of both active and return electrodes employed.

In one embodiment, the plasma conditions provide for a plasma media that flows in a laminar form within plasma device 12.

Figure 8:
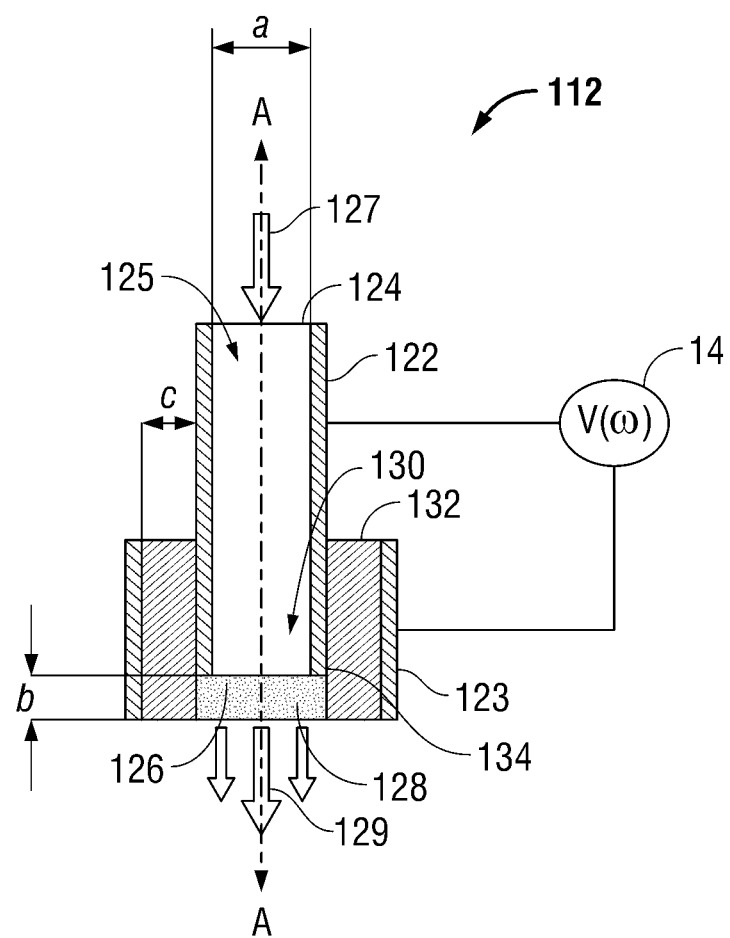
FIG. 8 is a perspective, cross-sectional view of a plasma device according to the present disclosure.

FIG. 8 shows a plasma device 112 includes an inner electrode 122 having a substantially cylindrical tubular shape having an opening 125 defined therethrough. The inner electrode 122 has a distal end 126 and proximal end 124 that is coupled to the ionizable media source 16 and the precursor source 18 (FIG. 1). The inner electrode 122 is also coupled to a porous member 128 at the distal end 126. The porous member 128 disperses the plasma passing through the inner electrode 122 to generate a wide-area plasma effluent 129. The inner electrode 122 may have an inner diameter a of 10 cm or less. The porous member 128 may be formed from sintered or metal glass, ceramic mesh, and other porous materials suitable for dispersion of gas. The porous member 128 may have a thickness b from about 0.1 to about 1.0 cm.

The plasma device 112 also includes an outer electrode 123 that also has a substantially cylindrical tubular or annular shape having a larger diameter than the diameter of the inner electrode 122. The inner and outer electrodes 122 and 123 are concentrically disposed about a longitudinal axis A-A. The outer electrode 123 has a shorter length than the inner electrode 122 and is disposed coaxially about the inner electrode 122. In particular, the outer electrode 123 encloses a distal portion 130 of the inner electrode 122 and the porous member 128.

The electrodes 122 and 123 may be formed from an electrically conductive or semi-conducting material suitable for ignition of plasma such as metals and metal-ceramic composites. In one embodiment, the electrodes 122 and 123 may be formed from a conductive metal including a native oxide or nitride compound disposed thereon.

The plasma device 112 also includes a dielectric spacer 132 having puck-like or toroidal shape. The dielectric spacer 132 includes an opening 134 through the center thereof that is adapted for insertion of the inner electrode 122 therethrough. The dielectric spacer 132 is disposed between the inner and outer electrodes 122 and 123. In one embodiment, the dielectric spacer 132 may be frictionally fitted to the electrodes 122 and 123 to secure the inner electrode 122 within the outer electrode 123. The dielectric spacer may have a thickness c from about 0.1 to about 1.0 cm (e.g., gauge). In one illustrative embodiment, the electrode spacer 132 may be formed from a dielectric material, such as a thin ceramic, to provide capacitive coupling between the inner and outer electrodes 122 and 123.

One of the electrodes 122 and 123 may be an active electrode and the other may be a neutral or return electrode to facilitate in RF energy coupling. Each of the electrodes 122 and 123 are coupled to the power source 14 that drives plasma generation, such that the energy from the power source 14 may be used to ignite and sustain the plasma in feedstocks 127 flowing through the device 112 (e.g., through the opening 125).

Figure 9:
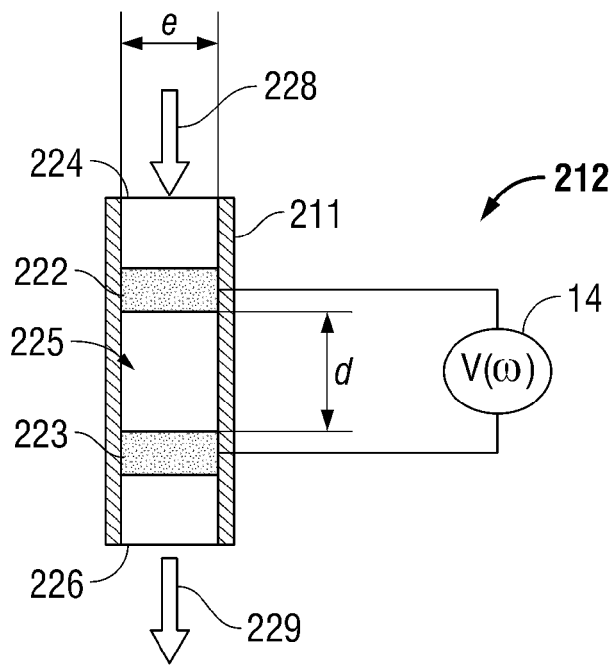
FIG. 9 is a perspective, cross-sectional view of a plasma device according to the present disclosure.

FIG. 9 shows another illustrative embodiment of a plasma device 212 which includes a housing 211 enclosing a first electrode 222 and a second electrode 223 separated by a predetermined distance d, which may be from about 0.1 cm to about 1 cm. The first electrode 222 is proximal of the second electrode 223 with respect to the supplied plasma feedstocks. The housing 211 has a substantially cylindrical tubular shape having an opening 225 defined therethrough. The housing 211 is formed from a dielectric material that insulates the first and second electrodes 222 and 223. The housing 211 may have an inner diameter e of 10 cm or less.

The plasma device 212 includes a distal end 226 and proximal end 224 that is coupled to the ionizable media source 16 and the precursor source 18. The first and second electrodes 222 and 223 are formed from conductive porous material, such as metal, metal-ceramic and semi-conducting composite meshes, porous sintered solids, and the like to permit the flow of plasma feedstocks 228 therethrough. The first and second electrodes 222 and 223 disperse the plasma passing through the housing 211 to generate a dispersed wide-area plasma effluent 229.

One of the electrodes 222 and 223 may be an active electrode and the other may be a neutral or return electrode to facilitate in RF energy coupling. Each of the electrodes 222 and 223 are coupled to the power source 14 that drives plasma generation, such that the energy from the power source 14 may be used to ignite the plasma feedstocks flowing through the device 212. The electrodes 222 and 223 are separated by a predetermined distance and are capacitively or inductively coupled through the plasma effluent 229 and the housing 211. More specifically, the ionizable media and the precursors flow through the device 212 through the chambered opening 225. As energy is applied to the electrodes 222 and 223, the plasma feedstocks are ignited to form the plasma effluent 229.

Figure 10:
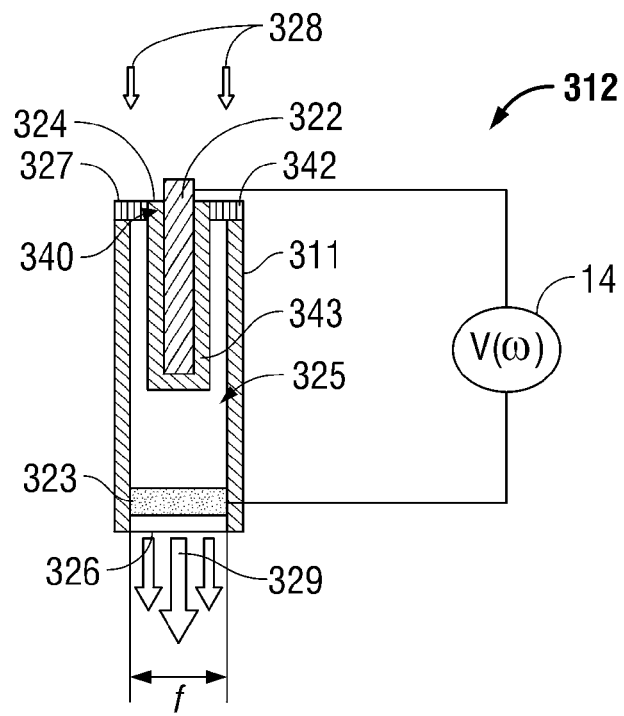
FIG. 10 is a perspective, cross-sectional view of a plasma device according to the present disclosure.

FIG. 10 shows another illustrative embodiment of a plasma device 312 which includes a housing 311 enclosing a first electrode 322 and a second electrode 323. The housing 311 has a substantially cylindrical tubular shape having a chambered opening 325 defined therethrough. The housing 311 is formed from a dielectric material that insulates the first and second electrodes 322 and 323. The housing 311 may have an inner diameter f of 10 cm or less.

The plasma device 312 includes a distal end 326 and proximal end 324 that is coupled to the ionizable media source 16 and the precursor source 18. The first electrode 322 may be a cylindrical rod formed from a conductive metal (e.g., aluminum alloy) or semiconductive material, disposed coaxially within the housing 311.

The plasma device 312 also includes an electrode spacer 327 disposed between first electrode 322 and the housing 311. The electrode spacer 327 is substantially similar to the electrode spacer 27 and may include a central opening 340 adapted for insertion of the inner electrode 322 therethrough and one or more flow openings 342 disposed radially around the central opening to allow for the flow of plasma feedstocks 328 (e.g., ionizable media and precursors) through the device 312. The electrode spacer 327 may be frictionally fitted to the housing 311 and the first electrode 322 to secure the first electrode 22 within the housing 311. In one illustrative embodiment, the electrode spacer 327 may be formed from a dielectric material, such as ceramic. In another embodiment, the electrode spacer 327 may be formed integrally with the housing 311.

The first electrode 322 also includes an insulative layer 343, which may be formed integrally with the housing 311 and the electrode spacer 327. In another illustrative embodiment, the layer 343 may be formed from a dielectric material deposited as a film unto or grown on the inner conductor via processes including, but not limited to, sputtering, chemical vapor (e.g., atomic layer deposition, evaporation, electrochemical methods, or ion implantation.). The insulative layer 343 may also be a native metal oxide or nitride if the first electrode 332 is formed from a suitable alloy, such as aluminum and titanium. In particular, the first electrode 322 may be formed from an aluminum alloy and the layer 342 may be aluminum oxide ($Al_2O_3$) or aluminum nitride (AlN). In another illustrative embodiment, the first electrode 322 may be formed from a titanium alloy and the layer 342 may be titanium oxide ($TiO_2$) or titanium nitride (TiN).

The second electrode 323 is formed from a conductive or semiconductive porous material, such as metal and metal-ceramic composite meshes, porous sintered solids and the like to permit the flow of plasma feedstocks 328 therethrough. The second electrode 323 also disperses the plasma passing through the housing 311 to generate a wide-area plasma effluent 329.

One of the electrodes 322 and 323 may be an active electrode and the other may be a neutral or return electrode to facilitate in RF energy coupling. Each of the electrodes 322 and 323 are coupled to the power source 14 that drives plasma generation, such that the energy from the power source 14 may be used to ignite the plasma feedstocks flowing through the device 312. The electrodes 322 and 323 are capacitively or inductively coupled through the plasma effluent 329 and the housing 311. More specifically, the ionizable media and the precursors flow through the device 312 through the chambered opening 325. As energy is applied to the electrodes 322 and 323, the plasma feedstocks are ignited to form the plasma effluent 329.

Figure 11A:
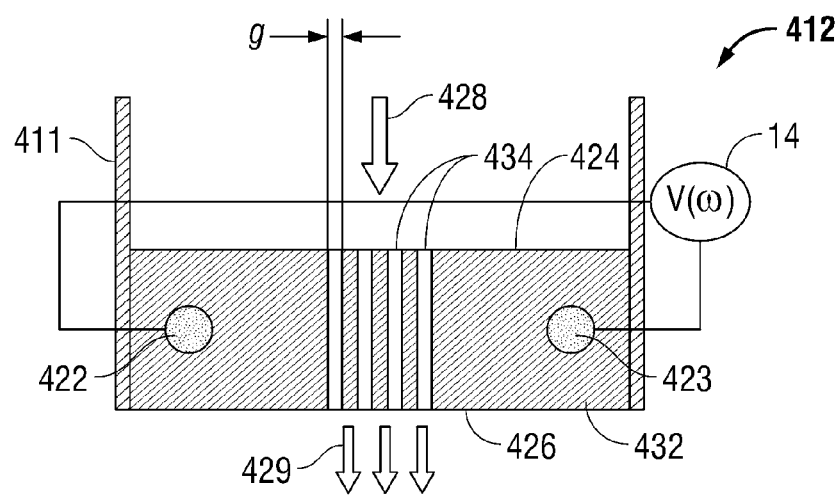
FIG. 11A is a perspective, cross-sectional view of a plasma device according to the present disclosure.
Figure 11B:
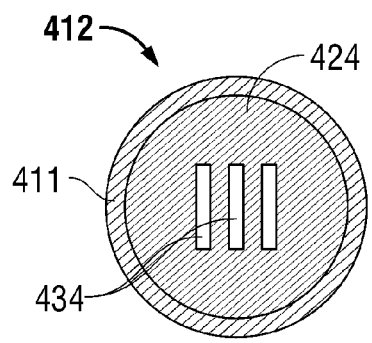
FIG. 11B is a top view of a plasma device of FIG. 11A according to the present disclosure.
Figure 11C:
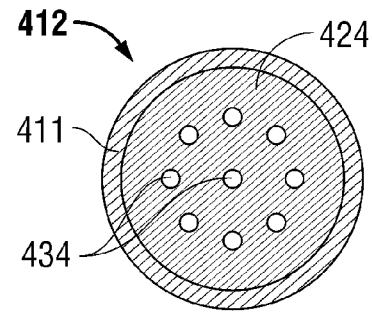
FIG. 11C is a top view of a plasma device of FIG. 11B according to the present disclosure.

FIGS. 11A-C show another illustrative embodiment of a plasma device 412 which includes a housing 411 and a dielectric spacer 432 having disk-like or toroidal shape disposed within the housing 411. The dielectric spacer 432 may be frictionally fitted to the housing 411. In one illustrative embodiment, the dielectric spacer 432 may be formed integrally with the housing 411.

The dielectric spacer 432 includes a bottom surface 426 and a top surface 424 that is coupled to the ionizable media source 16 and the precursor source 18 (FIG. 1). The electrode spacer 432 may be formed from a dielectric material, such as ceramic, plastic, and the like. The dielectric spacer 432 includes one or more openings 434 through the center thereof to allow for the flow of plasma feedstocks 428 therethrough. In one illustrative embodiment, the dielectric spacer 432 may be formed from a porous dielectric media suitable for allowing gases to flow therethrough thereby obviating the need for openings 434. The multiple openings 434 and/or porous nature of the dielectric spacer 432 provide for dispersion of the plasma passing therethrough to generate a wide-area plasma effluent 429. The openings 434 may be of various shapes and sizes. FIG. 11B shows the openings 434 as slits formed in the dielectric spacer 432. FIG. 11C shows the openings 434 as substantially cylindrical lumens. At its widest thickness g, the openings 434 may be from about 0.1 cm to about 1.0 cm.

The plasma device 412 also includes first and second electrodes 422 and 423 disposed within the dielectric spacer 432. The first and second electrodes 422 and 423 may be cylindrical rods, formed from a conductive metal (e.g., aluminum alloy) and may be inserted into the dielectric spacer 432 in parallel configuration and equidistant from the center of the dielectric spacer 432. The dielectric spacer 432 provides capacitive coupling between the inner and outer electrodes 422 and 423. In one embodiment electrodes 422 and 423 may have one or more regions that form and present sharpened protuberances toward openings 434 to increase the local electric fields.

One of the electrodes 422 and 423 may be an active electrode and the other may be a neutral or return electrode to facilitate in RF energy coupling. Each of the electrodes 422 and 423 are coupled to the power source 14 that drives plasma generation, such that the energy from the power source 14 may be used to ignite the plasma feedstocks flowing through the device 412. The electrodes 422 and 423 are capacitively coupled through the plasma effluent 429 and the dielectric spacer 432. More specifically, the ionizable media and the precursors flow through the device 412 through the openings 434. As energy is applied to the electrodes 422 and 423, the plasma feedstocks are ignited to form the plasma effluent 429.

Figure 12A:
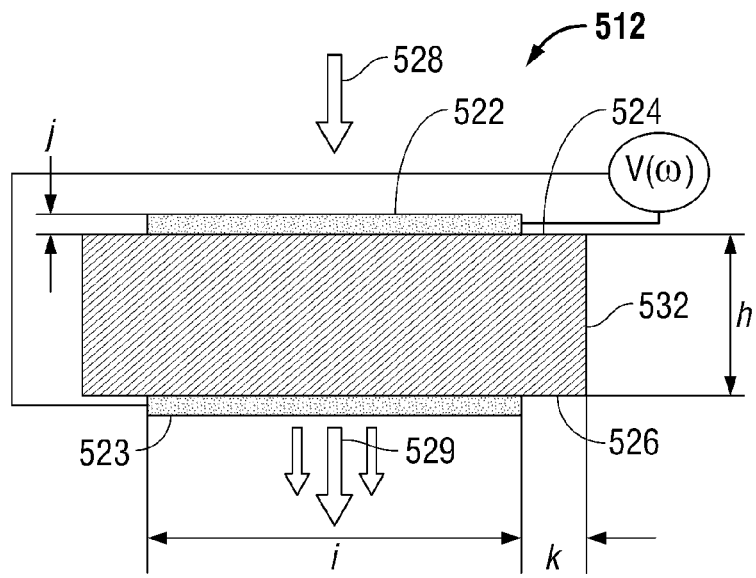
FIG. 12A is a perspective, cross-sectional view of a plasma device according to the present disclosure.
Figure 12B:
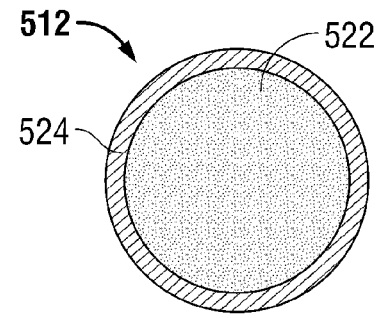
FIG. 12B is a top view of a plasma device of FIG. 12A according to the present disclosure.

FIGS. 12A-B show another illustrative embodiment of a plasma device 512 which includes a dielectric spacer 532 having a substantially disk shape. The plasma device 512 includes a bottom surface 526 and a top surface 524 that is coupled to the ionizable media source and the precursor source 18 (FIG. 1). The electrode spacer 532 may be formed from a dielectric material, such as ceramic, plastic, and the like. In one illustrative embodiment, the dielectric spacer 532 may be formed from a porous dielectric media suitable for allowing gases to flow therethrough, or otherwise have open ports to allow flow of plasma feedstocks 528 through the plasma device 512. The electrode spacer 532 may have a thickness h from about 0.1 cm to about 1.0 cm.

The plasma device 512 also includes first and second electrodes 522 and 523. The first and second electrodes 522 and 523 may also have a disk or plate shape and are disposed on the top and bottom surfaces 524 and 526, respectively. The first and second electrodes 522 and 523 are formed from a conductive or semiconductive porous material, such as metal and metal-ceramic composite meshes, porous sintered solids, and the like to permit the flow of plasma feedstocks 528 therethrough, or otherwise have open ports to allow flow of plasma feedstocks 528 through the plasma device 512. The first and second electrodes 522 and 523 may have a diameter i from about 0.1 cm to about 1.0 cm and a thickness j from about 0.1 cm to about 1.0 cm.

The dielectric spacer 532 may have a larger diameter extending outside the periphery of the first and second electrodes 522 and 523, such that a border k is formed, which may be from about 0.1 cm to about 1.0 cm. This configuration enhances capacitive coupling between the inner and outer electrodes 522 and 523. One or both of electrodes 522 and 523 may also be formed into predetermined surface shapes and features to induce effects such as inductive coupling. The porous nature of the dielectric spacer 532 in conjunction with the first and second electrodes 522 and 523 provides for dispersion of the plasma passing therethrough to generate a wide-area plasma effluent 529.

One of the electrodes 522 and 523 may be an active electrode and the other may be a neutral or return electrode to facilitate in RF energy coupling. Each of the electrodes 522 and 523 are coupled to the power source 14 that drives plasma generation, such that the energy from the power source 14 may be used to ignite the plasma feedstocks 528 flowing through the device 512. The ionizable media and the precursors flow through the device 512 and as energy is applied to the electrodes 522 and 523, the plasma feedstocks are ignited to form the plasma effluent 529.

Figure 13:
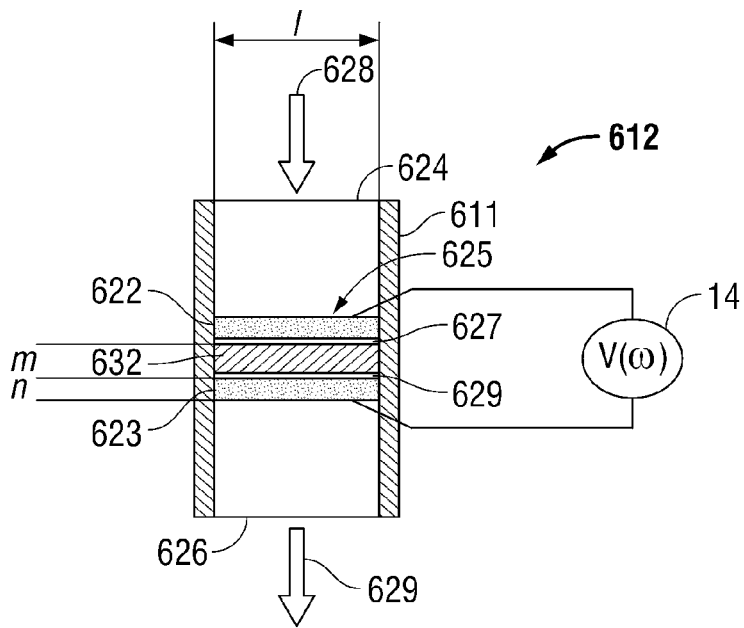
FIG. 13 is a perspective, cross-sectional view of a plasma device according to the present disclosure.

FIG. 13 shows another illustrative embodiment of a plasma device 612, which is a combination of the plasma device 212 of FIG. 9 and plasma device 512 of FIG. 12. The plasma device 612 includes a housing 611 enclosing a dielectric spacer 632 having disk shape, a first electrode 622 and a second electrode 623. The housing 611 may have an inner diameter l of 10 cm or less. The plasma device 612 includes a bottom surface 626 and a top surface 624 that is coupled to the ionizable media source 16 and the precursor source 18 (FIG. 1). The dielectric spacer 632 may be formed from a dielectric material, such as ceramic, plastic, and the like. In one illustrative embodiment, the dielectric spacer 632 may be formed from a porous dielectric media suitable for allowing gases to flow therethrough. The dielectric spacer 632 has a thickness m from about 0.1 cm to about 1.0 cm.

The first and second electrodes 622 and 623 may also have a disk or plate shape and are disposed on the top and bottom surfaces 627 and 629, respectively. The first and second electrodes 622 and 623 have a thickness n from about 0.1 cm to about 1.0 cm and are formed from a conductive porous material, such as metal and metal-ceramic composite meshes, porous sintered solids, and the like to permit the flow of plasma feedstocks 628 therethrough. The porous nature of the dielectric spacer 632 in conjunction with the first and second electrodes 622 and 623 provides for dispersion of the plasma passing therethrough to generate a wide-area plasma effluent 629. The dielectric spacer 632 also provides for capacitive coupling between the inner and outer electrodes 622 and 623.

One of the electrodes 622 and 623 may be an active electrode and the other may be a neutral or return electrode to facilitate in RF energy coupling. Each of the electrodes 622 and 623 are coupled to the power source 14 that drives plasma generation, such that the energy from the power source 14 may be used to ignite and sustain the plasma feedstocks 628 flowing through the device 612. In one embodiment one electrode may be a solid and the second electrode formed into a spiral or other highly inductive form to achieve inductive coupling. The ionizable media and the precursors 628 flow through the device 612 and as energy is applied to the electrodes 622 and 623, the plasma feedstocks are ignited to form the plasma effluent 629.

Figure 14:
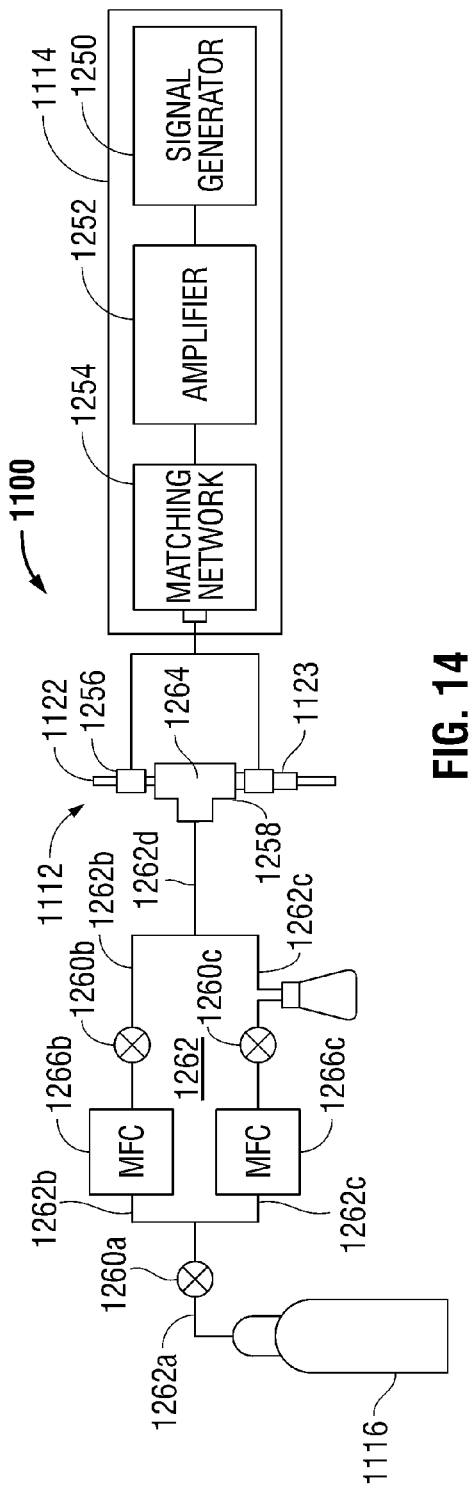
FIG. 14 is a schematic diagram of a plasma system according to one embodiment of the present disclosure.
Figure 15:
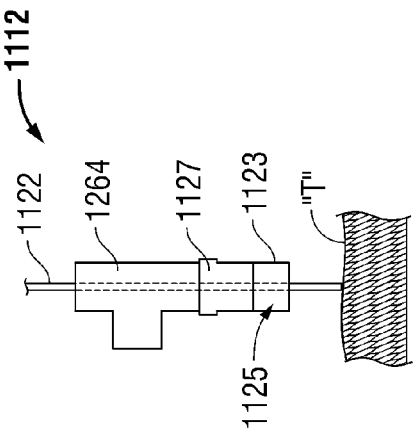
FIG. 15 is a side, cross-sectional view of a plasma device according to the present disclosure.

FIGS. 14 and 15 show an illustrative embodiment of a plasma system 1100. The system 1100 includes a plasma device 1112 that is coupled to a power source 1114, an ionizable media source 1116 and a precursor source 1118. Power source 1114 includes a signal generator 1250 coupled to an amplifier 1252. The signal generator 1250 outputs a plurality of control signals to the amplifier 1252 reflective of the desired waveform. The signal generator 1250 allows for control of desired waveform parameters (e.g., frequency, duty cycle, amplitude, pulsing, etc.). In some embodiments, signal generator 1250 may pulse the waveform, e.g., a continuous-wave waveform signal may be switched on and off at a duty cycle (the duty cycle may be fixed or variable) and at a different frequency from the frequency of the continuous-wave waveform. The amplifier 1252 outputs the desired waveform at a frequency from about 0.1 MHz to about 2,450 MHz and in another embodiment from about 1 MHz to about 13.56 MHz. The power source 1114 also includes a matching network 1254 coupled to the amplifier 1252. The matching network 1254 may include one or more reactive and/or capacitive components that are configured to match the impedance of the load (e.g., plasma effluent) to the power source 1114 by switching the components or by frequency tuning.

The power source 1114 is coupled to a plasma device 1112. As shown in FIG. 15, the plasma device 1112 may be utilized for application of plasma to tissue. The device 1112 includes an inner electrode 1122, which may be an aluminum alloy rod, disposed coaxially within an outer electrode 1123. The outer electrode 1123 may be an aluminum alloy tube having an opening 1125. As shown in FIG. 14, the inner and outer electrode 1122 and 1123 are coupled to the power source 1114 via connectors 1256 and 1258, which are disposed around the inner electrode 1122 and 1123, respectively. The connectors 1256 and 1258 may be copper connector blocks.

With reference to FIG. 15, the device 1112 also includes a ceramic electrode spacer 1127 disposed between the inner and outer electrodes 1122 and 1123. The electrode spacer 1127 may be disposed at any point between the inner and outer electrodes 1122 and 1123 to provide for a coaxial configuration between the inner and outer electrodes 1122 and 1123. The electrode spacer 1127 is substantially similar to the electrode spacer 27 and may include a central opening (not explicitly shown) adapted for insertion of the inner electrode 1122 therethrough and one or more flow openings (not explicitly shown) disposed radially around the central opening to allow for the flow of plasma feedstocks through the device 1112. The electrode spacer 1127 may be frictionally fitted to the electrodes 1122 and 1123 to secure the inner electrode 1122 within the outer electrode 1123. One of the electrodes 1122 and 1123 may be an active electrode and the other may be a neutral or return electrode to facilitate in RF energy coupling.

With reference to FIG. 14, the plasma system 1100 also includes an ionizable media source 1116 and a precursor source 1118 coupled to the plasma device 1112. The ionizable media source 1116 provides ionizable feedstock, namely, helium gas, to the plasma device 1112. The ionizable media source 1116 includes a storage tank for storing the helium gas. The ionizable media source 1116 is coupled to the precursor source 1118 via tubing 1262, which includes tubing 1262a coupled to the ionizable media source 1116. The tubing 1262a branches into tubing 1262b and 1262c. The tubing 1262c is coupled to the precursor source 1118, which may be a bubbler or a nebulizer, for aerosolizing precursor feedstocks, namely liquid hydrogen peroxide, prior to introduction thereof into the device 1112. The feedstocks are mixed upstream of the device 1112 prior to introduction thereto.

The tubing 1262b bypasses the tubing 1262c and reconnects at tubing 1262d, which is coupled to the plasma device 1112 at a coupling 1264. The coupling 1264 may be a Teflon union tee connected to the outer electrode 1123. The tubing 1262 also includes valves 1260a, 1260b, 1260c which control the flow of the helium gas and the hydrogen peroxide through the tubing 1262a, 1262b, 1262c, respectively. The tubing 1262 further includes mass flow controllers 1266b and 1266c adapted to control the flow of plasma feedstocks through the tubing 1260b and 1260c, respectively.

The system 1100 provides a flow of plasma through the device 1112 to the tissue. Plasma feedstocks, which include helium gas and hydrogen peroxide, are supplied by the ionizable media source 1116 and the precursor source 1118, respectively, to the plasma device 1112, which are ignited to form plasma effluent containing ions, radicals, photons from the specific excited species and metastables that carry internal energy to drive desired chemical reactions with the tissue or at the surface thereof.

Figure 16:
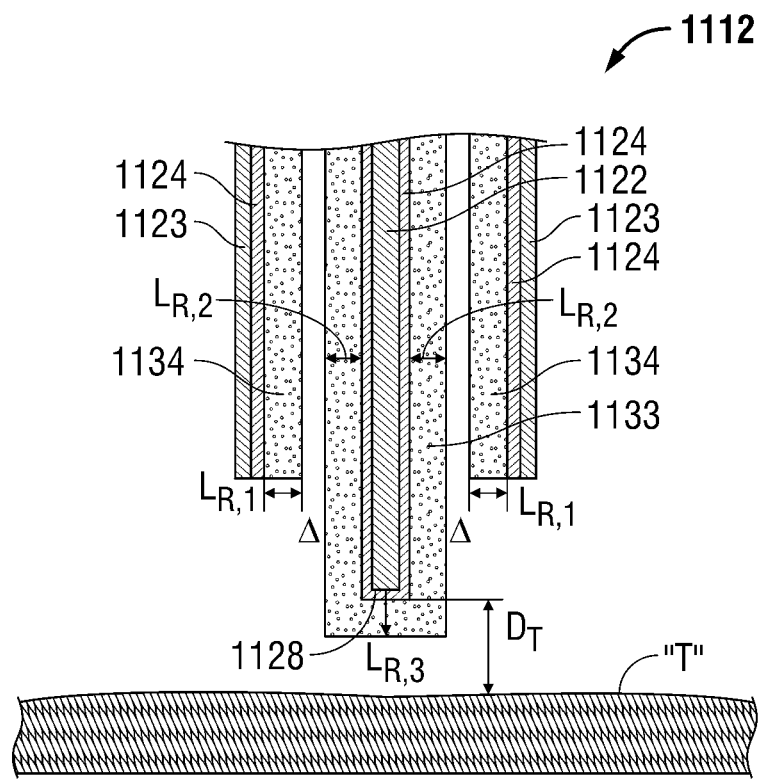
FIG. 16 is a close-up, side view of a plasma device according to the present disclosure.

With reference to FIG. 16, a close-up, side view of a plasma device 1112 according to the present disclosure. Plasma device 1112 includes the inner electrode 1122 and the outer electrode 1123. The plasma device 1112 also includes a coating 1124 disposed on the outer surface of the inner electrode 1122 and on the inner surface of the outer electrode 1123. The coating 1124 is substantially similar to the coating 24 that is discussed above with respect to FIGS. 4-6. In one embodiment, the plasma device 1112 may also include additional features discussed above with respect to FIGS. 4-6 such as grooves disposed in a parallel or spiral configurations, nanostructure pores filled with precursor materials, and/or vents within the inner electrode 1122. In another embodiment, the inner electrode 1122 may be disposed in a variety of configurations and spatial orientation with respect to the outer electrode 1123. In particular, the inner electrode 1122 may be recessed, flush or extended relative to the outer electrode 1123 as shown in FIGS. 2B-2D. The extended distance of the inner electrode 1122 may also be adjustable as discussed above with respect to FIGS. 2A-2D.

FIG. 16 illustrates working ranges $L_{R,1}$, $L_{R,2}$ and $L_{R,3}$, and a distance $D_T$. Outer electrode 1123 includes a working range $L_{R,1}$ of energetic secondary electron emissions. Inner electrode 1122 includes working ranges $L_{R,2}$, and $L_{R,3}$ of energetic secondary electron emissions having energy E. In other words, the working ranges are representative of the thickness of energetic electron sheath layers 1133 and 1134, which are disposed about the inner and outer electrodes 1122 and 1123, respectively. A gap distance $\Delta$ shows the zone where the concentration of energetic secondary electrons is relatively lower. Coating the electrodes, as discussed above, reduces gap distance $\Delta$. In some embodiments, distance $\Delta$ may be reduced to zero and/or working ranges $L_{R,1}$ and $L_{R,2}$ may overlap thereby creating an hollow cathode effect. Inner electrode 1112 includes a tip 1128 having a distance $D_T$ from tissue "T". Ranges $L_{R,1}$, $L_{R,2}$ and $L_{R,3}$, indicate regions with a greatly increased concentration of electrons with relatively high energies that drive reactions in the gas phase. As discussed above, the coating 1124 on electrodes 1122 and/or 1123 can increase or enhance working ranges $L_{R,1}$ and $L_{R,2}$, and/or $L_{R,3}$ of energetic secondary electrons. Thus, varying the thickness of the coating 1124 can be used to adjust the working ranges $L_{R,1}$ and $L_{R,2}$, and/or $L_{R,3}$. Additionally or alternatively, the distance $D_T$ that tip 1128 is disposed from tissue "T" is adjustable to achieve a predetermined tissue effect (discussed in more detail below).

$$R(E) = \sigma(E) \cdot n_e(E) \cdot v(E). \tag{3}$$

Formula (3) relates the reaction rate R that indicates an inelastic (energy expending) collision where an electron at energy E, e(E), interacts with gas particle X. As a result of the collision the electron may transfer energy to X. After the collision, the electron and particle will have different energies. The rate or efficiency of this reaction is controlled by the energy dependent cross-section $\sigma(E)$ of the particular reaction.

Figure 17A:
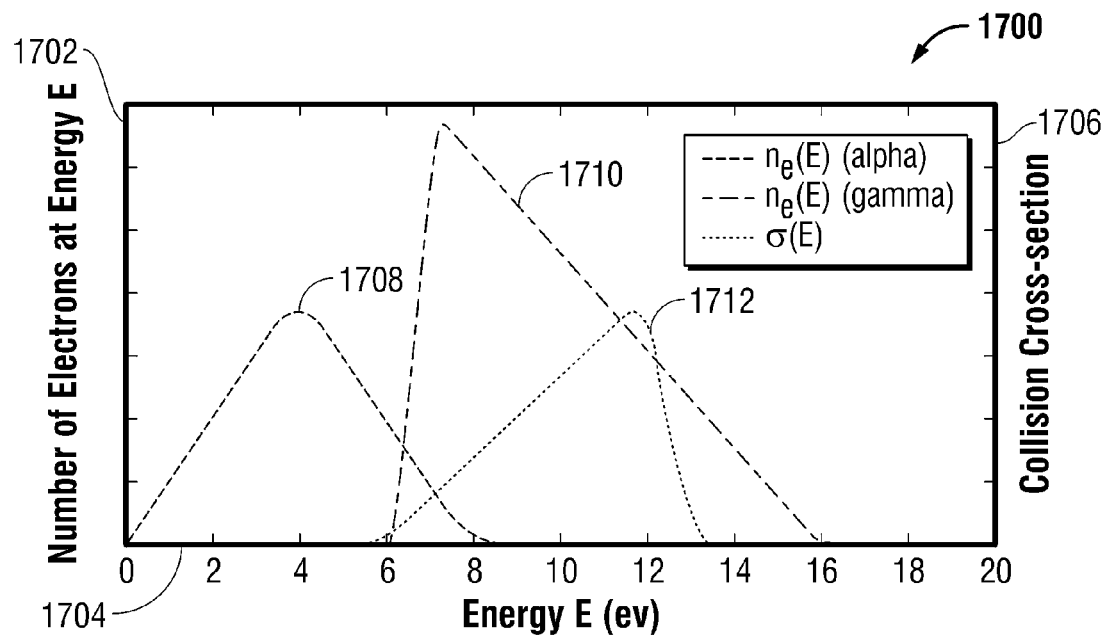
FIGS. 17A and 17B are plots relating to electron emissions according to the present disclosure.
Figure 17B:
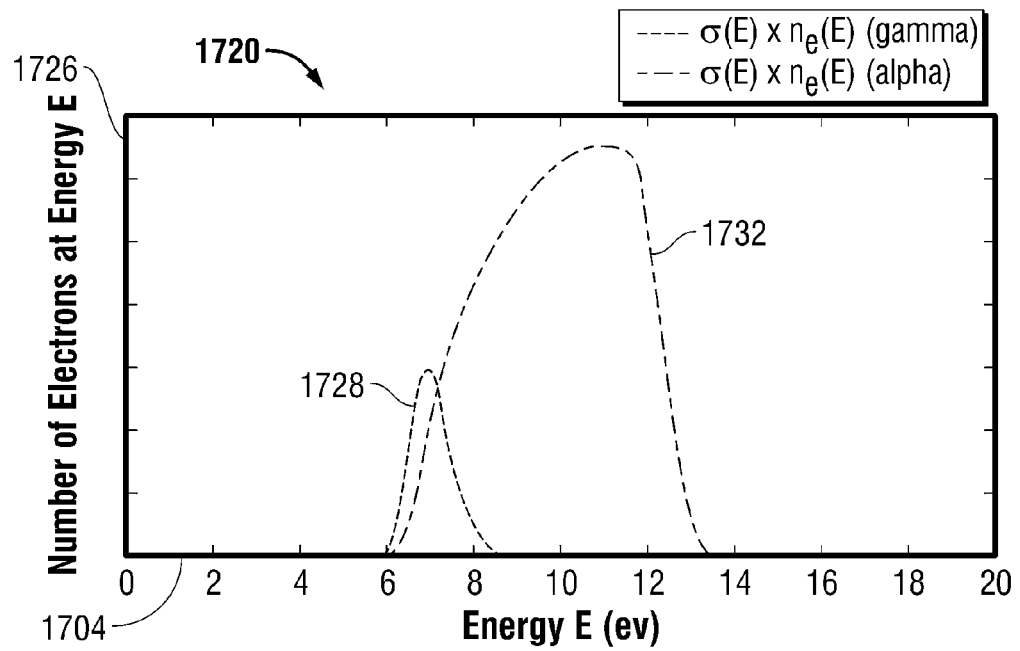

Referring now to FIGS. 17A and 17B that show two plots, respectively. FIG. 17A shows a plot 1700 illustrating typical electron concentrations $n_e(E)$ versus energy for alpha-mode and gamma-mode discharges, and a typical collisional reaction cross-section. Plot 1700 includes axes 1702, 1704, and 1706. Axis 1702 shows the number of electrons at energy E (i.e., a distribution). Axis 1704 shows energy E of electrons in electron-volts (eV). Line 1708 illustrates the number of electrons at energy E (axis 1702) versus energy E (axis 1704) as would be found in an alpha-mode discharge. Line 1712 illustrates the number of electrons at energy E (axis 1702) versus energy E (axis 1704) as would be found in a gamma-mode discharge, which results from enhancement of secondary emission in the gamma-mode discharge. The probability of a collisional reaction between an electron and a gas particle depends on the reaction cross-section, $\sigma(E)$, a general form of which is shown here as a function of energy E (axis 1704) as line 1710. Line 1710 shows the collision cross-section (axis 1706) versus Energy E (axis 1704).

Referring now to FIG. 17B, plot 1720 shows the calculated point-by-point multiplication product of $\sigma(E) \cdot n_e(E)$, a numeric indication of chemical reaction probability, for each mode of discharge. Plot 1702 includes an axis 1726 indicating the reaction probability at energy E. Line 1728 shows the product $\sigma(E) \cdot n_e(E)$ for an alpha-mode discharge as a function of energy E (axis 1704). Line 1732 shows the product $\sigma(E) \cdot n_e(E)$ for a gamma-mode discharge as a function of energy E (axis 1704). The overall reaction rate for each mode of discharge is related to the integral of each line (the area under each line). The reaction rate is given by the product of this quantity and the velocity distribution v(E), specifically $\sigma(E) \cdot n_e(E) \cdot v(E)$. The components of the product of FIG. 17B are shown in FIG. 17A. Line 1728 indicates the point-by-point multiplication (convolution) of lines 1708 and 1710, and line 1732 indicates the convolution of lines 1712 and 1710.

Referring again to FIG. 17A, line 1708 shows peak alpha electron emissions occurring at point 1708, and may correspond to an electron-voltage of about 1 eV to about 3 eV. The majority of chemical bonds and/or chemical reactions with the electrons occur within an energy range of about 2 eV to about 10 eV. Line 1710 shows the likelihood of $n_e(E)$ with additional secondary electron emissions. This illustrates that the secondary electron emissions increase the probability that chemical reactions of feedstocks with electrons to form reactive radicals occur with tissue "T" within an energy range of secondary electron emissions.

Referring again to FIG. 16, plasma device 1112 is shown with inner electrode 1128 disposed a distance $D_T$ from tissue "T". Distance $D_T$ corresponds to the magnitudes of various physicals effects, each energetic physical effect affecting directivity, selectivity, heating and other aspects of the tissue processing of tissue "T". For $D_T \gg L_{R,3}$ the secondary electrons do not reach the tissue surface. FIGS. 18A-18C include charts illustrating the contributing physical effects affecting tissue "T" as a function of distance $D_T$ that inner electrode 1128 is disposed from tissue "T" (see FIG. 16).

FIGS. 18A and 18B illustrate the chemical effect, heating effect, and a blend of the two as a mixture effect that the plasma device 1112 has on tissue "T" (see FIG. 16). For $D_T > L_{R,3}$ more energetic secondary electrons in volume enhance chemical reactions for the chemical effect and the mixture effect, but produce minimal or no heating effect. As shown in FIG. 18A, impinging secondary electrons on the tissue surface enhance chemical reactions both in the gas volume and at the tissue surface. Secondary electron emissions also enhance tissue surface reactions when $D_T < L_{R3}$ but do not have electron stimulated surface reactions when $D_T < L_{R3}$. In summary for the energetic secondary electron emissions to enhance tissue surface reactions, the condition of formula (4) must be satisfied as follows:

$$0 < D_T \leq L_{R,3} \tag{4}$$

FIG. 18A also shows a condition during which the inner electrode 1122 touches tissue "T" (see FIG. 16) therefore making $D_T < 0$. When the inner electrode 1122 touches tissue "T", chemical effects are mostly blocked, while bulk heating effects are enhanced. This case is mostly dominated by $I^2R$ or $j^2 \rho$ (Ohmic) heating. When inner electrode 1122 touches tissue "T", the inner electrode thermally conducts heat to the tissue. Additionally, inner electrode 1122 is capacitively coupled to Tissue "T" (when touching) and electrically conducts energy thereto. Also, when inner electrode 1122 touches the tissue, the reacted tissue is moved away exposing un-reacted tissue.

With reference to FIG. 18B, a chart illustrating effects of coating is shown. Coatings enhance secondary electron emissions, thereby increasing radical fluxes and energetic electrons as well as facilitate the surface heating effect. The electrode coating 1124 increases radical densities to enhance tissue reactions at surfaces for the chemical effect. For the heating effect, the electrode coating 1124 increases radical, secondary and electron flux to enhance surface reactions on tissue.

With reference to FIG. 18C, various effects of disposing inner electrode 1122 in spaced relation to tissue are illustrated. Although, FIG. 18C refers to the inner electrode 1122, in some embodiments, the outer electrode 1124 may be disposed in spaced relation to the tissue "T", both electrodes 1122 and 1124 may be disposed in spaced relation to the tissue "T", or the sheath having a working range $L_{R,1}$ may be disposed in spaced relation to tissue "T". Additionally or alternatively, one or more of plasma devices plasma device as described with reference to any one of FIG. 1 through 16 may be combined with the teachings of with FIGS. 18A-18C and may be chosen to achieve a target tissue effect or result. Anyone one or more of the chemical effect, the heating effect, the directivity, the selectivity, or any other effect as described in FIG. 18C may be selected as a desired (or target) effect, and a plasma device as described with reference to any one of FIG. 1 through 16 (or equivalents or combinations thereof), the plasma device's position in relation to tissue "T", and/or the power applied to the plasma device may be adjusted or controlled for to achieve the desired tissue effect(s).

FIG. 18C will be described as follows with reference to plasma device 1112 of FIG. 16. When the electron sheaths are not in contact with tissue "T" (e.g., the sheath having working range $L_{R,3}$) the heating effect is minimal (or no effect), the chemical effect is limited by lateral diffusion loss away from the tissue, directionality is present due to gas transport, and selectivity is present and is chemistry dominated. When the sheath is in contact with tissue, the heating effect is small or limited, the chemical effect is strong (both chemical and electron flux effects), directionality is strongest (both gas transport and electron flux), and selectivity is strong (both chemical and electron flux effects). When the inner electrode 1122 touches tissue "T," the heating effect is a strong effect, the chemical effect is present but is reduced at the tissue-electrode interface, there is some directionality, and there is some selectivity on the sides but is reduced at the tissue-electrode interface. When the center electrode (e.g., inner electrode 1122) extends into tissue, the heating effect is maximum, the chemical effect is limited (or minimal), the electrode shape dominates directionality, and for selectivity: the thermal effects dominate and there is some selectivity on the sides When the inner electrode 1122 extends into tissue or otherwise touches tissue "T", the inner electrode 1122 transfers thermal energy to the tissue and is capacitively coupled to the tissue thereby conducting electricity through tissue "T".

Figure 19:
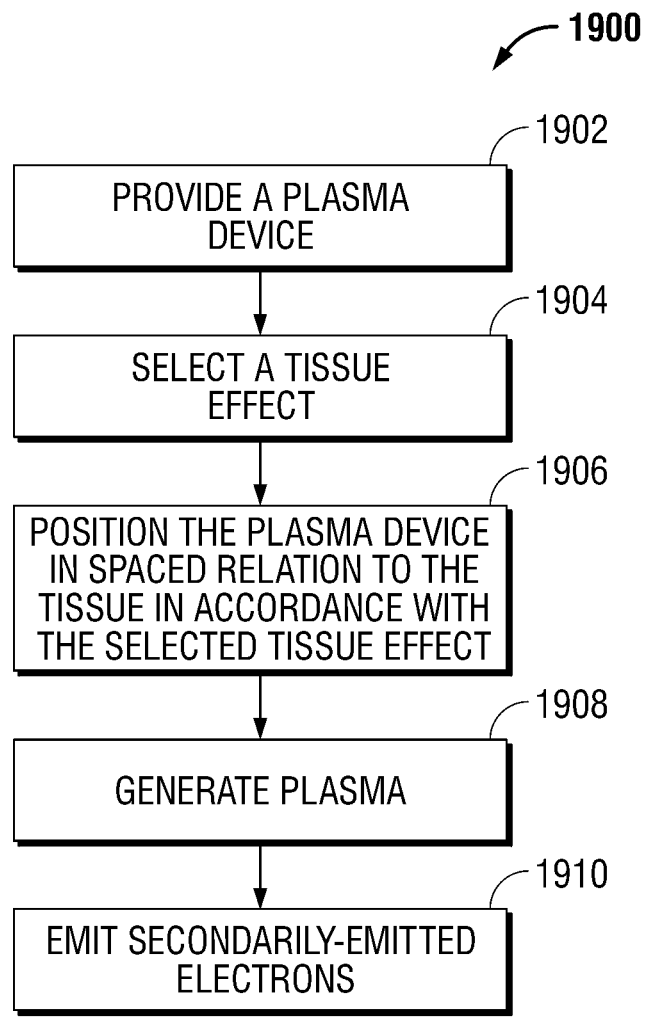
FIG. 19 is a flow chart diagram of a method of plasma tissue treatment according to the present disclosure.

With reference to FIG. 19, a method 1900 for treating tissue is shown according to the present disclosure. Step 1902 provides a plasma device. Step 1904 selects a tissue effect. The tissue effect of step 1904 may be a heating effect, a chemical effect and/or a mixture effect as described above with respect to the FIG. 18A. Step 1906 positions the plasma device in spaced relation to the tissue in accordance with the selected tissue effect. Step 1908 generates plasma. Step 1910 emits secondarily emitted electrons via secondary electron emissions. The secondary electrons may be controlled to achieve one or more magnitudes of one or more selected tissue effects.

Figure 20:
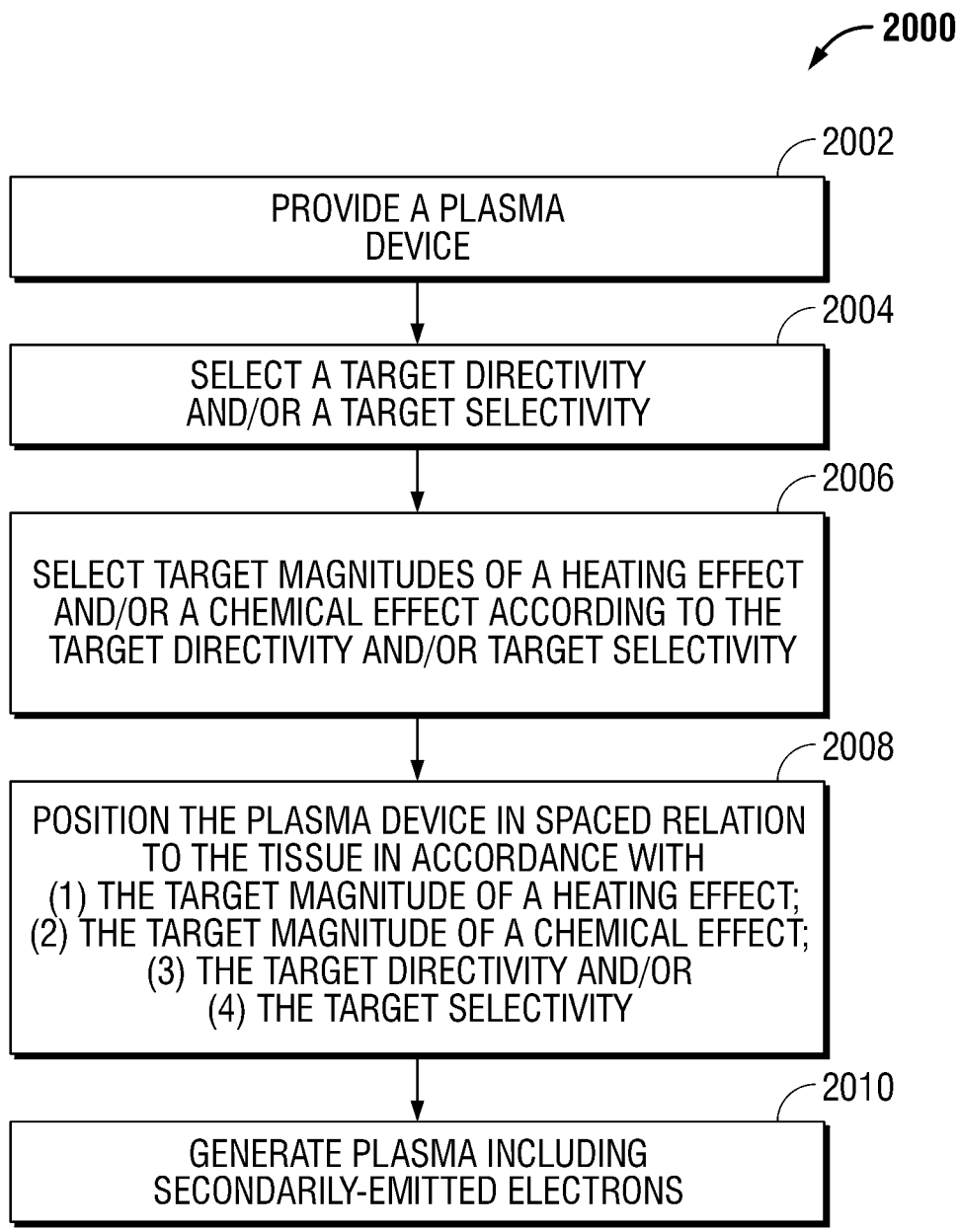
FIG. 20 is a flow chart diagram of another method of plasma tissue treatment according to the present disclosure.

With reference to FIG. 20, a flow chart diagram of a method 2000 of plasma tissue treatment is illustrated according to the present disclosure. Step 2002 provides a plasma device. Step 2004 selects a target directivity and/or a target selectivity as described above with respect to the FIG. 18C. Directional secondary electrons predominately impinge on the bottom, as opposed to the sidewalls, of the tissue cuts. Preferential irradiation of the bottom results in a directional tissue removal. Choice of chemical radical flux and tissue type change the tissue removal rate, allowing the removal of one tissue type but not another. Selectivity between tissue types >15 are achievable.

Step 2006 selects target magnitudes of a heating effect and/or a chemical effect according to the target directivity and/or target selectivity. Step 2008 positions the plasma device in spaced relation to tissue in accordance with (1) the target magnitude of a heating effect; (2) the target magnitude of a chemical effect; (3) the target directivity; and/or (4) the target selectivity. The selected relative magnitudes of the surface heating and chemical effects may be a function of the selected directivity and/or selectivity. Step 2010 generates a plasma including energetic secondarily emitted electrons which may ($D_T$<$L_{R3}$) or may not ($D_T$>$L_{R3}$) impinge on the tissue surface.

EXAMPLE 1

Figure 21:
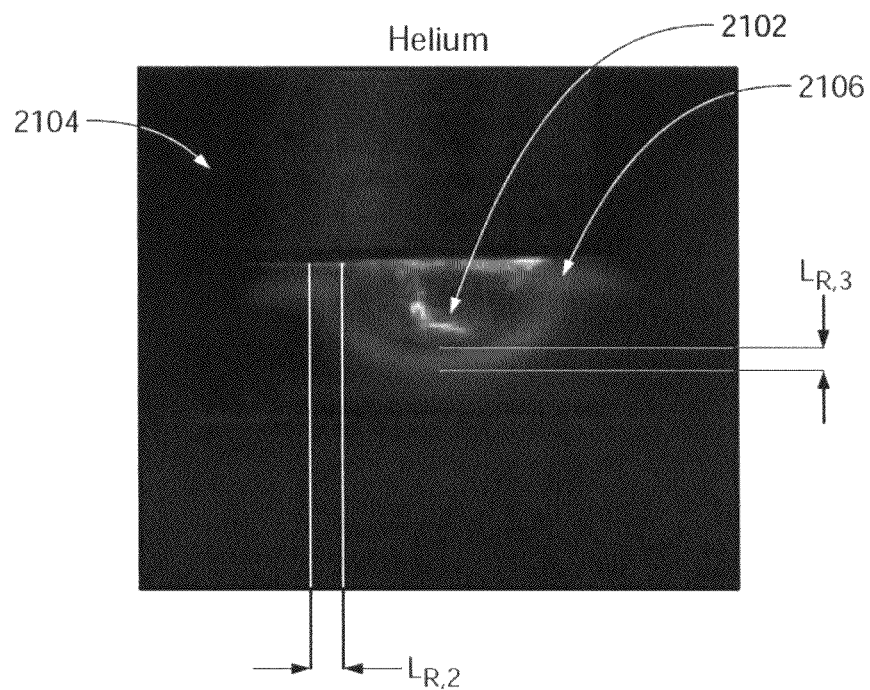
FIG. 21 shows a gray-scale photograph of a plasma discharge according to the present disclosure.

For example 1, refer to FIG. 21 showing a gray-scale photograph of an example of plasma discharge having drawings thereon showing various regions according to the present disclosure. FIG. 21 shows an inner electrode 2102, an outer electrode 2104, and an energetic electron sheath layer 2106. The working ranges $L_{R,2}$ and $L_{R,3}$ are identified. The energetic electron sheath layer 2106 was photographed as having a generally purple color around a region about inner electrode 2102. The general thickness of the generally-purple energetic electron sheath layer 2106 had a thickness of about $L_{R,3}$ near the distal end of inner electrode 2102 and a thickness of about $L_{R,2}$ in the region where electron sheath 2106 begins to extend to within outer electrode 2104. The plasma system was setup as shown in FIGS. 14 and 15 utilizing Helium gas as ionizable media, which has a relatively high $\sigma_{Ar}(E)$ resulting in small $L_{R3}$ and at location $D_T$ and lack of secondary electrons, due to a relatively high electron collision cross section of Helium atoms. The $\sigma_{Feedstock}(E)$ for the feedstock chemistry acts in the same way.

EXAMPLE 2

Figure 22:
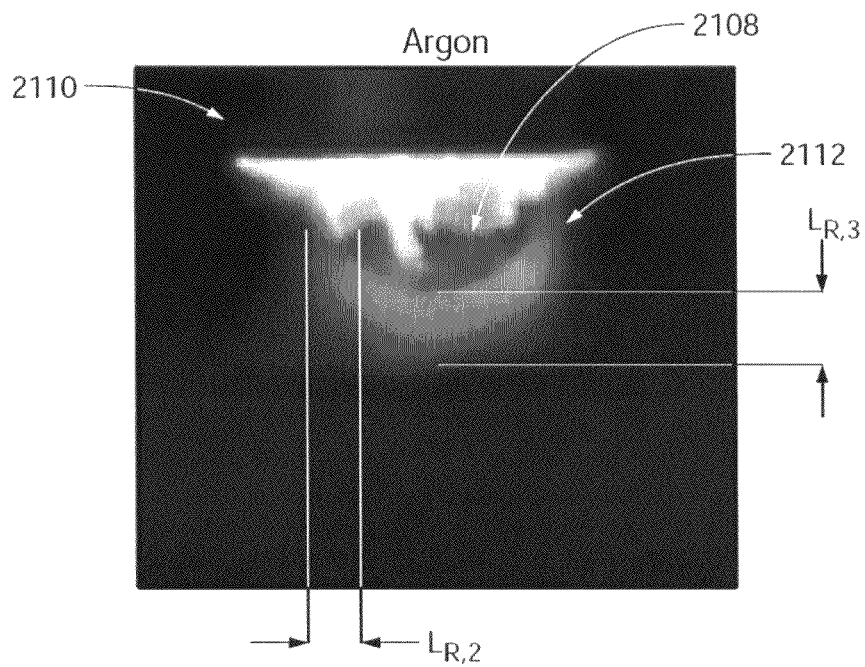
FIG. 22 shows a gray-scale photograph of another plasma discharge according to the present disclosure.

For example 2, refer to FIG. 22 showing a color photograph of an example of plasma discharge having drawings thereon showing various regions according to the present disclosure. FIG. 22 shows an inner electrode 2108, an outer electrode 2110, and an energetic electron sheath layer 2112. The working ranges $L_{R,2}$ and $L_{R,3}$ are identified. The energetic electron sheath layer 2112 was photographed as having a generally orange-like color around a region about inner electrode 2108. The general thickness of the generally orange-like energetic electron sheath layer 2112 had a thickness of about $L_{R,3}$ near the distal end of inner electrode 2108 and a thickness of about $L_{R,2}$ in the region where energetic electron sheath layer 2106 begins to extend to within outer electrode 2110. The plasma system was setup as shown in FIGS. 14 and 15 utilizing Argon gas as ionizable media, which has a relatively low $\sigma$, resulting in a large $L_{R3}$ and at location $D_T$ an abundance of energetic secondary electrons. The plasma effluent included a orange-like sheath layer in the extended region $L_{R3}$ that is brighter and bigger than the $L_{R3}$ of Example 1, which indicates more efficient excitation of gas atoms due to increased collisions with energetic electrons. In addition, the plasma effluent included a congruent larger orange-like layer that is believed to be produced by the energetic electrons within working distance $L_{R3}$.

Although the illustrative embodiments of the present disclosure have been described herein with reference to the accompanying drawings, it is to be understood that the disclosure is not limited to those precise embodiments, and that various other changes and modifications may be effected therein by one skilled in the art without departing from the scope or spirit of the disclosure. Another example is overlapping working distances $L_{R1}$ and $L_{R2}$ which causes hollow cathode enhancement of the radical flux density in the volume and RF at the surface. In particular, as discussed above this allows the tailoring of the relative populations of plasma species to meet needs for the specific process desired on the workpiece surface or in the volume of the reactive plasma.

What is claimed is:

1. A plasma system, comprising:
a plasma device including:
an outer electrode having an inner surface and a first coating including a first type of material, the first coating disposed on at least a portion of the inner surface; and
an inner electrode disposed within the outer electrode and having an outer surface and a second coating including a second type of material different from the first type of material, the second coating disposed on at least a portion of the outer surface;
an ionizable media source coupled to the plasma device and configured to supply ionizable media thereto; and
a power source coupled to the inner electrode and the outer electrode and configured to ignite the ionizable media to form a plasma effluent having an electron sheath layer about a distal end portion of the inner electrode.

2. The plasma system according to claim 1, wherein the first type of material is a catalyst, and the second type of material is configured to promote increased secondary electron emission.

3. The plasma system according to claim 1, wherein the plasma device defines an opening between the outer surface of the inner electrode and the inner surface of the outer electrode.

4. The plasma system according to claim 1, wherein the inner electrode and the outer electrode are formed from an alloy, and the first type of material and the second type of material include at least one of an oxide or a nitride of the alloy of the inner electrode or the outer electrode.

5. The plasma system according to claim 4, further comprising a precursor source coupled to the plasma device and configured to provide at least one of an oxygen or a nitrogen to the plasma device to replenish at least one of the first type of material or the second type of material.

6. The plasma system according to claim 1, wherein at least one of the first coating or the second coating includes a plurality of nanostructure pores.

7. The plasma system according to claim 6, wherein at least a portion of the plurality of nanostructure pores includes precursor feedstock disposed therein.

8. The plasma system according to claim 1, wherein the inner surface of the outer electrode defines a plurality of grooves therein, the plurality of grooves having the first coating disposed therein.

9. The plasma system according to claim 1, wherein the distal end portion of the inner electrode extends distally past a distal end of the outer electrode, the second coating covering the inner electrode up to the distal end portion of the inner electrode such that the distal end portion of the inner electrode is un-insulated.

10. The plasma system according to claim 1, wherein the plasma device further includes an electrode spacer slidably disposed between the inner electrode and the outer electrode.

11. A plasma device configured to receive ionizable media, comprising:
an outer electrode having an inner surface and a first coating including a first type of material, the first coating disposed on at least a portion of the inner surface; and
an inner electrode disposed within the outer electrode and having an outer surface and a second coating including a second type of material different from the first type of material, the second coating disposed on at least a portion of the outer surface.

12. The plasma device according to claim 11, wherein the first type of material is a catalyst, and the second type of material is configured to promote increased secondary electron emission.

13. The plasma device according to claim 11, wherein an opening is defined between the outer surface of the inner electrode and the inner surface of the outer electrode.

14. The plasma device according to claim 11, wherein the inner electrode and the outer electrode are formed from an alloy, and the first type of material and the second type of material are formed from at least one of an oxide or a nitride of the alloy of the inner electrode or the outer electrode.

15. The plasma device according to claim 11, wherein at least one of the first coating or the second coating includes a plurality of nanostructure pores.

16. The plasma device according to claim 15, wherein the plurality of nanostructure pores includes precursor feedstock disposed therein.

17. The plasma device according to claim 11, wherein the inner surface of the outer electrode defines a plurality of grooves therein, the plurality of grooves having the first coating disposed therein.

18. The plasma device according to claim 11, wherein the inner electrode includes a distal end portion extending distally past a distal end of the outer electrode, the second coating covering the inner electrode up to the distal end portion of the inner electrode such that the distal end portion of the inner electrode is un-insulated.

* * * * *